United States Patent [19]
Caldwell et al.

[11] Patent Number: 5,932,551
[45] Date of Patent: Aug. 3, 1999

[54] SUBSTITUTED N-CARBOXYALKYLPEPTIDYL DERIVATIVES AS ANTIDEGENERATIVE ACTIVE AGENTS

[75] Inventors: Charles G. Caldwell; Kevin T. Chapman, both of Scotch Plains; Craig K. Esser, Keasbey; William K. Hagmann, Westfield; Ihor E. Kopka, Millburn, all of N.J.; Scott A. Polo, Yardley, Pa.; Soumya P. Sahoo, Old Bridge; Philippe L. Durette, New Providence, both of N.J.

[73] Assignee: Merck & Co., Inc., Rahway, N.J.

[21] Appl. No.: 08/848,766

[22] Filed: May 1, 1997

Related U.S. Application Data

[63] Continuation of application No. 08/533,879, Sep. 26, 1995, abandoned, which is a continuation of application No. 08/397,538, Mar. 2, 1995, abandoned, which is a continuation of application No. 07/873,905, Apr. 24, 1992, abandoned.

[51] Int. Cl.$^6$ .................................................. A61K 38/05
[52] U.S. Cl. .............................. 514/19; 514/18; 530/331; 562/445; 562/575
[58] Field of Search ........................ 514/18, 19; 530/331; 562/445, 575

[56] References Cited

U.S. PATENT DOCUMENTS 4,771,037 9/1988 Roberts ..................................... 514/18

FOREIGN PATENT DOCUMENTS 0079521 5/1983 European Pat. Off. .

OTHER PUBLICATIONS

Chu *Biochemistry* 23, 3598, 1984.
Fletcher, et al, Am. Chem. Soc., Advances in Chemistry Series 126 pp. 311–317 (1974).
Moore, et al, Assay for Evaluation of Proteoglycanolytic Activity of Proteinases in the Rabbit Articular Joint–Quantitation of Proteoglycanases In Vivo.
McDonnell, et al, Arthritis and Rheumatism, vol. 35, No. 7 (Jul. 1992) pp. 799–805.
K.T. Chapman, et al., Journ. Med. Chem., 36: 4293–4301 (1993) Inhibition of Matrix Metalloproteinases by N–Carboxyalkyl Peptides.
American Chem. Soc., "Nomenclature of Organic Compounds—Principles and Practice", No. 126, 1974, pp. 311–312.
Biochemical Pharmacology, vol. 36, No. 7, 1987 pp. 995–1002, Pergamon Journals Ltd; C.B. Caputo, et al.: "Proteoglycan degradtion by a chondrocyte Metalloptrotease".
Proceedings of the Society for Experimental Biology and Medicine, vol. 183, 1986, pp. 262–267, G. DiPasquale, et al.: "Proteoglycan– and Collagen–Degrading Enzymes from Human Interleukin 1–. . . ".

*Primary Examiner*—Cecilia J. Tsang
*Assistant Examiner*—David Lukton
*Attorney, Agent, or Firm*—Richard C. Billups; Curtis C. Panzer; David L. Rose

[57] ABSTRACT

Novel N-carboxyalkylpeptidyl compounds of formula I are found to be useful inhibitors of matrix metalloendoproteinase-mediated diseases including osteoarthritis, rheumatoid arthritis, septic arthritis, tumor invasion in certain cancers, periodontal disease, corneal ulceration, proteinuria, dystrophobic epidermolysis bullosa, and coronary thrombosis associated with atherosclerotic plaque rupture. The matrix metalloendoproteinases are a family of zinc-containing proteinases including but not limited to stromelysin, collagenase, and gelatinase, that are capable of degrading the major components of articular cartilage and basement membranes. The inhibitors claimed herein may also be useful in preventing the pathological sequelae following a traumatic injury that could lead to a permanent disability. These compounds may also have utility as a means for birth control by preventing ovulation or implantation.

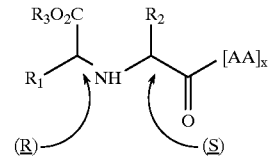

I

14 Claims, No Drawings

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 11 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

Arg Pro Lys Pro Gln Gln Phe Phe Gly Leu Met
1               5                   10

(2) INFORMATION FOR SEQ ID NO:2:

(i) SEQUENCE CHARACTERISTICS:
      (A) LENGTH: 6 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:2:

Pro Leu Gly Xaa Leu Gly
1               5

SUBSTITUTED N-CARBOXYALKYLPEPTIDYL DERIVATIVES AS ANTIDEGENERATIVE ACTIVE AGENTS

This application is a continuation of application Ser. No. 08/533,879, filed Sep. 26, 1995, now abandoned, which is a continuation of application Ser. No. 08/397,538, filed Mar. 2, 1995, now abandoned, which is a continuation of application Ser. No. 07/873,905, filed Apr. 24, 1992, now abandoned.

BACKGROUND OF THE INVENTION

Novel N-carboxyalkylpeptidyl compounds of formula I are found to be useful inhibitors of matrix metalloendoproteinase-mediated diseases including osteoarthritis, rheumatoid arthritis, septic arthritis, tumor invasion in certain cancers, periodontal disease, corneal ulceration, proteinuria, dystrophobic epidermolysis bullosa, and coronary thrombosis associated with atherosclerotic plaque rupture. The matrix metalloendoproteinases are a family of zinc-containing proteinases including but not limited to stromelysin, collagenase, and gelatinase, that are capable of degrading the major components of articular cartilage and basement membranes. The inhibitors claimed herein may also be useful in preventing the pathological sequelae following a traumatic injury that could lead to a permanent disability. These compounds may also have utility as a means for birth control by preventing ovulation or implantation.

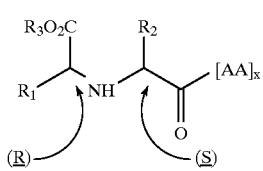

The disability observed in osteoarthritis (OA) and rheumatoid arthritis (RA) is largely due to the loss of articular cartilage. No therapeutic agent in the prior art is known to prevent the attrition of articular cartilage in these diseases.

"Disease modifying antirheumatic drugs" (DMARD), i.e., agents capable of preventing or slowing the ultimate loss of joint function in OA and RA are widely sought. Generic nonsteroidal antiinflammatory drugs (NSAIDs) may be combined with such agents to provide some relief from pain and swelling.

Stromelysin (aka. proteoglycanase, matrix metalloproteinase-3, MMP-3, procollagenase activator, "transin"), collagenase (aka. interstitial collagenase, matrix metalloproteinase-1), and gelatinase (aka. type IV collagenase, matrix metalloproteinase-2, MMP-2, 72 kDa-gelatinase or type V collagenase, matrix metalloproteinase-9, MMP-9, 95 kDa-gelatinase) are metalloendoproteinases secreted by fibroblasts and chondrocytes, and are capable of degrading the major connective tissue components of articular cartilage or basement membranes. Elevated levels of both enzymes have been detected in joints of arthritic humans and animals: K. A. Hasty, R. A. Reife, A. H. Kang, J. M. Stuart, "The role of stromelysin in the cartilage destruction that accompanies inflammatory arthritis", Arthr. Rheum., 33, 388–97 (1990); S. M. Krane, E. P. Amento, M. B. Goldring, S. R. Goldring, and M. L. Stephenson, "Modulation of matrix synthesis and degradation in joint inflammation", The Control of Tissue Damage", A. B. Glauert (ed.), Elsevier Sci. Publ., Amsterdam, 1988, Ch. 14, pp 179–95; A. Blanckaert, B. Mazieres, Y. Eeckhout, G. Vaes, "Direct extraction and assay of collagenase from human osteoarthrtic cartilage", Clin. Chim. Acta, 185 73–80 (1989). Each enzyme is secreted from these cells as an inactive proenzyme which is subsequently activated. There is evidence that stromelysin may be the in vivo activator for collagenase, implying a cascade for degradative enzyme activity: A. Ho, H. Nagase, "Evidence that human rheumatoid synovial matrix metalloproteinase 3 is an endogenous activator of procollagenase", Arch Biochem Biophys., 267, 211–16 (1988); G. Murphy, M. I. Crockett, P. E. Stephens, B. J. Smith, A. J. P. Docherty, "Stromelysin is an activator of procollagenase", Biochem. J., 248, 265–8 (1987). Inhibiting stromelysin could limit the activation of collagenase as well as prevent the degradation of proteoglycan.

That stromelysin inhibition may be effective in preventing articular cartilage degradation has been demonstrated in vitro by measuring the effect of matrix metalloendoproteinase inhibitors on proteoglycan release from rabbit cartilage explants: C. B. Caputo, L. A. Sygowski, S. P. Patton, D. J. Wolanin, A. Shaw, R. A. Roberts, G. DiPasquale, J. Orthopaedic Res., 6, 103–8 (1988).

There is an extensive literature on the involvement of these metalloproteinases in arthritis, but there is very little to guide one in developing a specific inhibitor for each enzyme.

In preliminary studies of rabbit proteoglycanase with substrates and inhibitors, little was found to indicate the enzyme's requirements for hydrolysis or inhibition beyond a preference for hydrophobic residues at the $P_1'$ position: A. Shaw, R. A. Roberts, D. J. Wolanin, "Small substrates and inhibitors of the metalloproteoglycanase of rabbit articular chondrocytes", Adv. Inflam. Res., 12, 67–79 (1988). More extensive studies with a series of substrates revealed that stromelysin will tolerate nearly every amino acid residue around the scissile bond: G. B. Fields, H. Brikedal-Hansen, H. E. Van Wart, unpublished results presented at the Matrix Metalloproteinase Conference, September 1989, Sandestin Fla.

Human rheumatoid synovial collagenase has been shown to share ~50% homology with human stromelysin: S. E. Whitham, G. Murphy, P. Angel, H. J. Rahmsdorf, B. J. Smith, A. Lyons, T. J. R. Harris, J. J. Reynolds, P. Herrlich, A. J. P. Docherty, "Comparison of human stromelysin and collagenase by cloning and sequence analysis", Biochem. J., 240, 913–6 (1986). Many collagenase inhibitors have been designed around the cleavage site of the α-chain sequence of Type II collagen: W. H. Johnson, N. A. Roberts, N. Brokakoti, "Collagenase inhibitors: their design and potential therapeutic use", J. Enzyme Inhib., 2,1–22 (1987). One such inhibitor, N-[3-(benzyloxycarbonyl)amino-1-carboxy-n-propyl]-L-leucyl-O-methyl-L-tyrosine, N-methylamide, prepared at G. D. Searle, Inc., and shown to be a potent inhibitor of human rheumatoid synovial collagenase ($IC_{50}$= 0.8 μM), was also found to inhibit rabbit bone proteoglycanase ($IC_{50}$=0.5 μM): J.-M. Delaisse, Y. Eeckhout, C. Sear, A. Galloway, K. McCullagh, G. Vaes, "A new synthetic inhibitor of mammalian tissue collagenase inhibits bone resorption in culture", Biochem. Biophys. Res. Commun., 133, 483–90 (1985).

Gelatinase (MR ~72,000) has been isolated from rheumatoid fibroblasts: Y. Okada, T. Morodomi, J. J. Enghild, K. Suzuki, A. Yasui, I. Nakanishi, G. Salvesen, H. Nagase, "Matrix metalloproteinase 2 from human rheumatoid synovial fibroblasts", Eur. J., Biochem., 194, 721–30 (1990).

The synthesis of the proenzyme is not coordinately regulated with the other two metalloproteinases and its activation may also be different. The role of gelatinase in the tissue destruction of articular cartilage appears different from the other two enzymes and, therefore, its inhibition may provide additional protection from degradation. A higher molecular weight gelatinase (MR ~95,000; aka. type-V collagenase, matrix metalloproteinase-9, MMP-9) is also secreted by fibroblasts and monocytes and may be involved in cartilage degradation.

As appreciated by those of skill in the art, the significant proportion of homology between human fibroblast collagenase, stromelysin, and gelatinase leads to the possibility that a compound that inhibits one enzyme may to some degree inhibit all of them.

Compounds that inhibit collagenase, which possess structural portions akin to those of the instant invention include those encompassed by U.S. Pat. No. 4,511,504 issued Apr. 16, 1985; U.S. Pat. No. 4,568,666, issued Feb 4, 1986.

Compounds of related structure that are claimed to inhibit stromelysin (proteoglycanase) are encompassed by U.S. Pat. No. 4,771,037, issued Sept. 13, 1988.

The applicants believe that stromelysin and collagenase inhibitors have utility in preventing articular cartilage damage associated with septic arthritis. Bacterial infections of the joints can elicit an inflammatory response that may then be perpetuated beyond what is needed for removal of the infective agent resulting in permanent damage to structural components. Bacterial agents have been used in animal models to elicit an arthritic response with the appearance of proteolytic activities. See J. P. Case, J. Sano, R. Lafyatis, E. F. Remmers, G. K. Kumkumian, R. L. Wilder, "Transin/stromelysin expression in the synovium of rats with experimental erosive arhtritis", J. Clin Invest., 84, 1731–40 (1989); R. J. Williams, R. L. Smith, D. J. Schurman, "Septic Arthritis: Staphylococcal induction of chondrocyte proteolytic activity", Arthr. Rheum., 33, 533–41 (1990).

The applicants also believe that inhibitors of stromelysin, collagenase, and gelatinase will be useful to control tumor metastasis, optionally in combination with current chemotherapy and/or radiation. See L. M. Matrisian, G. T. Bowden, P. Krieg, G. Furstenberger, J. P. Briand, P. Leroy, R. Breathnach, "The mRNA coding for the secreted protease transin is expressed more abundantly in malignant than in benign tumors", Proc. Natl. Acad. Sci., USA, 83, 9413–7 (1986); S. M. Wilhelm, I. E. Collier, A. Kronberger, A. Z. Eisen, B. L. Marmer, G. A. Grant, E. A. Bauer, G. I. Goldberg, "Human skin fibroblast stromelysin: structure, glycosylation, substrate specificity, and differential expression in normal and tumorigenic cells", Ibid., 84, 6725–29 (1987); Z. Werb et al., Signal transduction through the fibronectin receptor induces collagenase and stromelysin gene expression, J. Cell Biol., 109, 872–889 (1989); L. A. Liotta, C. N. Rao, S. H. Barsky, "Tumor invasion and the extracellular matrix", Lab. Invest., 49, 636–649 (1983); R. Reich, B. Strafford, K. Klein, G. R. Martin, R. A. Mueller, G. C. Fuller, "Inhibitors of collagenase IV and cell adhesion reduce the invasive activity of malignant tumor cells", in Metastasis: Ciba Foundation Symposium; Wiley, Chichester, 1988, pp. 193–210.

Secreted proteinases such as stromelysin, collagenase, and gelatinase play an important role in processes involved in the movement of cells during metastasic tumor invasion. Indeed, there is also evidence that the matrix metalloproteinases are overexpressed in certain metastatic tumor cell lines. In this context, the enzyme functions to penetrate underlying basement membranes and allow the tumor cell to escape from the site of primary tumor formation and enter circulation. After adhering to blood vessel walls, the tumor cells use these same metalloendoproteinases to pierce underlying basement membranes and penetrate other tissues, thereby leading to tumor metastasis. Inhibition of this process would prevent metastasis and improve the efficacy of current treatments with chemotherapeutics and/or radiation.

These inhibitors should also be useful for controlling periodontal diseases, such as gingivitis. Both collagenase and stromelysin activities have been isolated from fibroblasts isolated from inflammed gingiva: V. J. Uitto, R. Applegren, P. J. Robinson, "Collagenase and neutral metalloproteinase activity in extracts of inflamed human gingiva", J. Periodontal Res., 16, 417–424(1981). Enzyme levels have been correlated to the severity of gum disease: C. M. Overall, O. W. Wiebkin, J. C. Thonard, "Demonstration of tissue collagenase activity in vivo and its relationship to inflammation severity in human gingiva", J. Periodontal Res., 22, 81–88 (1987).

Proteolytic processes have also been observed in the ulceration of the cornea following alkali burns: S. I. Brown, C. A. Weller, H. E. Wasserman, "Collagenolytic activity of alkali-burned corneas", Arch. Opthalmol., 81, 370–373 (1969). Mercapto-containing peptides do inhibit the collagenase isolated from alkali-burned rabbit cornea: F. R. Burns, M. S. Stack, R. D. Gray, C. A. Paterson, Invest. Opthalmol., 30, 1569–1575 (1989). Treatment of alkali-burned eyes or eyes exhibiting corneal ulceration as a result of infection with inhibitors of these metalloendoproteinases in combination with sodium citrate or sodium ascorbate and/or antimicrobials may be effective in preventing developing corneal degradation.

Stromelysin has been implicated in the degradation of structural components of the glomerular basement membrane (GBM) of the kidney, the major function of which is to restrict passage of plasma proteins into the urine; W. H. Baricos, G. Murphy, Y. Zhou, H. H. Nguyen, S. V. Shah, "Degradation of glomerular basement membrane by purified mammalian metalloproteinases", Biochem. J., 254, 609–612 (1988). Proteinuria, a result of glomerular disease, is excess protein in the urine caused by increased permeability of the GBM to plasma proteins. The underlying causes of this increased GBM permeability are unknown, but proteinases including stromelysin may play an important role in glomerular diseases. Inhibition of this enzyme may alleviate the proteinura associated with kidney malfunction.

It is suggested that inhibition of stromelysin activity may prevent the rupturing of atherosclerotic plaques leading to coronary thrombosis. The tearing or rupture of atherosclerotic plaques is the most common event initiating coronary thrombosis. Destabilization and degradation of the connective tissue matrix surrounding these plaques by proteolytic enzymes or cytokines released by infiltrating inflammatory cells has been proposed as a cause of plaque fissuring. Such tearing of these plaques can cause an acute thrombolytic event as blood rapidly flows out of the blood vessel. High levels of stromelysin RNA message have been found to be localized to individual cells in atherosclerotic plaques removed from heart transplant patients at the time of surgery: A. M. Henney, P. R. Wakeley, M. J. Davies, K. Foster, R. Hembry, G. Murphy, S. Humphries, "Localization of stromelysin gene expression in atherosclerotic plaques by in situ hybridization", Proc. Nat'l . Acad. Sci. USA, 88, 8154–8158 (1991). Inhibition of stromelysin by these compounds may aid in preventing or delaying the degradation of the connective tissue matrix that stabilizes the atherosclerotic plaques, thereby preventing events leading to acute coronary thrombosis.

It is also believed that specific inhibitors of stromelysin and collagenase should be useful as birth control agents. There is evidence that expression of metalloendoproteinases, including stromelysin and collagenase, is observed in unfertilized eggs and zygotes and at further cleavage stages and increased at the blastocyst stage of fetal development and with endoderm differentiation: C. A. Brenner, R. R. Adler, D. A. Rappolee, R. A. Pedersen, Z. Werb, "Genes for extracellular matrix-degrading metalloproteinases and their inhibitor, TIMP, are expressed during early mammalian development", Genes & Develop., 3, 848–59 (1989). By analogy to tumor invasion, a blastocyst may express metalloproteinases in order to penetrate the extracellular matrix of the uterine wall during implantation. Inhibition of stromelysin and collagenase during these early developmental processes should presumably prevent normal embryonic development and/or implantation in the uterus. Such intervention would constitute a novel method of birth control. In addition there is evidence that collagenase is important in ovulation processes. In this example, a covering of collagen over the apical region of the follicle must be penetrated in order for the ovum to escape. Collagenase has been detected during this process and an inhibitor has been shown to be effective in preventing ovulation: J. F. Woessner, N. Morioka, C. Zhu, T. Mukaida, T. Butler, W. J. LeMaire "Connective tissue breakdown in ovulation", Steroids, 54, 491–499 (1989). There may also be a role for stromelysin activity during ovulation: C. K. L. Too, G. D. Bryant-Greenwood, F. C. Greenwood, "Relaxin increases the release of plasminogen activator, collagenase, and proteo-glycanase from rat granulosa cells in vitro", Endocrin., 115, 1043–1050 (1984).

Collagenolytic and stromelysin activity have also been observed in dystrophobic epidermolysis bullosa: A. Kronberger, K. J. Valle, A. Z. Eisen, E. A. Bauer, J. Invest. Dermatol., 79 208–211 (1982); D. Sawamura, T. Sugawara, I. Hashimoto, L. Bruckmer-Tuderman, D. Fujimoto, Y. Okada, N. Utsumi, H. Shikata, Biochem. Biophys. Res. Commun., 174, 1003–8 (1991). Inhibition of metalloendoproteinases should limit the rapid destruction of connective components of the skin.

In addition to extracellular matrix comprising structural components, stromelysin can degrade other i vivo substrates including the inhibitors al-proteinase inhibitor and may therefore influence the activities of other proteinases such as elastase: P. G. Winyard, Z. Zhang, K. Chidwick, D. R. Blake, R. W. Carrell, G. Murphy, "Proteolytic inactivation of human $\alpha_1$-antitrypsin by human stromelysin", FEBS Letts., 279, 1, 91–94 (1991). Inhibition of the matrix metalloendoproteinases may potentiate the antiproteinase activity of these endogenous inhibitors.

SUMMARY OF THE INVENTION

The invention encompasses novel N-carboxy-alkylpeptidyl compounds of formula I which are useful inhibitors of matrix metalloendoproteinase-mediated diseases including degenerative diseases (such as defined above) and certain cancers.

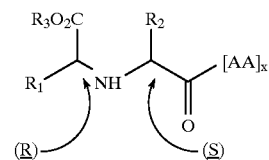

DETAILED DESCRIPTION OF THE INVENTION

The invention encompasses compounds of formula I.

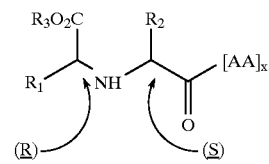

or a pharmaceutically acceptable salt thereof wherein:
$R_1$ is substituted $C_{1-6}$alkyl, wherein the substituent is selected from the group consisting of:
(a) hydrogen,
(b) carboxy,
(c)

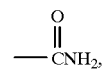

(d) $C_{6-10}$aryl wherein the aryl group is selected from the group consisting of
(1) phenyl,
(2) naphthyl,
(3) pyridyl,
(4) furyl,
(5) pyrryl,
(6) thienyl,
(7) isothiazolyl,
(8) imidazolyl,
(9) benzimidazolyl,
(10) tetrazolyl,
(11) pyrazinyl,
(12) pyrimidyl,
(13) quinolyl,
(14) isoquinolyl,
(15) benzofuryl,
(16) isobenzofuryl,
(17) benzothienyl,
(18) pyrazolyl,
(19) indolyl,
(20) isoindolyl,
(21) purinyl,
(22) carbazolyl,
(23) isoxazolyl,
(24) thiazolyl,
(25) oxazolyl,
(26) benzthiazolyl, and
(27) benzoxazolyl,
and mono and di-substituted $C_{6-10}$aryl as defined above in items (1) to (27) wherein the substitutents are independently selected from $C_{1-6}$alkyl, $C_{1-6}$alkyloxy, halo, hydroxy, amino, $C_{1-6}$alkylamino, amino$C_{1-6}$alkyl, carboxyl, carboxyl$C_{1-6}$alkyl, and $C_{1-6}$alkylcarbonyl;

(e)

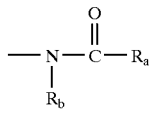

wherein $R_a$ and $R_b$ are each independently hydrogen; $C_{6-10}$aryl and mono and di-substituted $C_{6-10}$aryl as defined above (d); or substituted $C_{1-6}$alkyl wherein the substitutent is selected from hydroxy, halo, and phenyl, or wherein Ra and Rb are joined such that together with the nitrogen and carbon atoms to which they are attached, there is formed a lactam or benzolactam ring wherein the lactam portion thereof is a ring of up to 8 atoms, said lactam or benzolactam have a single hetero atom;

(f)

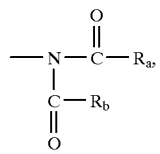

wherein $R_a$ and $R_b$ are each independently hydrogen; $C_{6-10}$aryl and mono and di-substituted $C_{6-10}$aryl as defined above (d); or substituted $C_{1-6}$alkyl wherein the substitutent is selected from hydroxy, halo, and phenyl, or wherein Ra and Rb are joined such that together with the nitrogen and carbon atoms to which they are attached, there is formed a lactim or benzolactim ring wherein the lactim portion thereof is a ring of up to 8 atoms, said lactim or benzolactim have a single hetero atom;

(g) amino and substituted amino wherein the substituent is selcted from $C_{1-6}$alkyl and $C_{6-10}$aryl wherein aryl is defined in (d);

$R_2$ is $CHR_cR_d$ wherein
$R_c$ is (a) H,
(b) $C_{1-3}$alkyl, or
(c) hydroxyl;
$R_d$ is $C_{6-10}$aryl$C_{1-2}$alkyl or $C_{6-10}$aryl substituted $C_{1-2}$alkyl wherein the substituent is $C_{1-3}$alkyl or hydroxy, and wherein the aryl group is selected from the group consisting of:
(1) phenyl,
(2) naphthyl,
(3) pyridyl,
(4) pyrryl,
(5) furyl,
(6) thienyl,
(7) isothiazolyl,
(8) imidazolyl,
(9) benzimidazolyl,
(10) tetrazolyl,
(11) pyrazinyl,
(12) pyrimidyl,
(13) quinolyl,
(14) isoquinolyl,
(15) benzofuryl,
(16) isobenzofuryl,
(17) benzothienyl,
(18) pyrazolyl,
(19) indolyl,
(20) isoindolyl,
(21) purinyl,
(22) carbazolyl,
(23) isoxazolyl,
(24) thiazolyl,
(25) oxazolyl,
(26) benzthiazolyl, and
(27) benzoxazolyl,
and mono and di-substituted $C_{6-10}$aryl as defined above in items (1) to (27) wherein the substitutents are independently selected from $C_{1-6}$alkyl, $C_{1-6}$alkyloxy, halo, hydroxy, amino, $C_{1-6}$alkylamino, amino$C_{1-6}$alkyl, carboxyl, carboxyl$C_{1-6}$alkyl, and $C_{1-6}$alkylcarbonyl;

$R_3$ is (a) H,
(b) $C_{1-10}$alkyl,
(c) $C_{6-10}$aryl or $C_{6-10}$aryl $C_{1-3}$alkyl, wherein the aryl group is selected from the group consisting of
(1) phenyl, and
(2) substituted phenyl, wherein the substitutent is carboxy, carboxy$C_{1-3}$alkyl, aminocarbonyl, $C_{1-6}$alkylaminocarbonyl;

AA is an amino acid of formula II

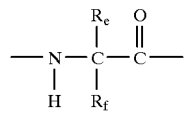

II wherein $R_e$ and $R_f$ are individually selected from:
(a) hydrogen,
(b) $C_{1-6}$alkyl,
(c) mercapto $C_{1-6}$alkyl,
(d) hydroxy $C_{1-6}$alkyl,
(e) carboxy $C_{1-6}$alkyl,
(f) amino substituted $C_{1-6}$alkyl
(g) aminocarbonyl $C_{1-6}$alkyl,
(h) mono- or di-$C_{1-6}$alkyl amino $C_{1-6}$alkyl,
(i) guanidino $C_{1-6}$alkyl,
(j) substituted phenyl $C_{1-6}$alkyl, wherein the substitutent is hydrogen, hydroxy, carboxy, $C_{1-4}$ alkyl, or $C_{1-4}$alkyloxy,
(k) substituted indolyl $C_{1-6}$alkyl, wherein the substitutent is hydrogen, hydroxy, carboxy, $C_{1-4}$ alkyl, or $C_{1-4}$alkyloxy,
(l) substituted imidazolyl $C_{2-6}$alkyl wherein the substitutent is hydrogen, hydroxy, carboxy, $C_{1-4}$alkyl, or $C_{1-4}$alkyloxy,
(m) substituted pyridyl $C_{1-6}$alkyl wherein the substitutent is hydrogen, hydroxy, carboxy, $C_{1-4}$ alkyl, or $C_{1-4}$alkyloxy,
(n) substituted pyridylamino $C_{1-6}$alkyl wherein the substitutent is hydrogen, hydroxy, carboxy, $C_{1-4}$ alkyl, or $C_{1-4}$alkyloxy, The above amino acids of formula II are intended to include but are not limited to glycine, alanine, valine, leucine, isoleucine, serine, threonine, aspartic acid, asparagine, glutamic acid, glutamine, lysine, hydroxylysine, arginine, homohistidine, phenylalanine, tyrosine, tryptophan, cysteine, methionine, ornithine, homoserine, and citrulline.

X is

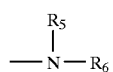

wherein $R_5$ and $R_6$ are each individually selected from the group consisting of:
(a) H,
(b) $C_{1-10}$alkyl,
(c) $C_{6-10}$aryl or $C_{6-10}$aryl $C_{1-6}$alkyl, wherein the aryl group is selected from the group consisting of
(1) phenyl,
(2) naphthyl,
(3) pyridyl,
(4) pyrryl,
(5) furyl,
(6) thienyl,
(7) isothiazolyl,
(8) imidazolyl,
(9) benzimidazolyl,
(10) tetrazolyl,
(11) pyrazinyl,
(12) pyrimidyl,
(13) quinolyl,
(14) isoquinolyl,
(15) benzofuryl,
(16) isobenzofuryl,
(17) benzothienyl,
(18) pyrazolyl,
(19) indolyl,
(20) isoindolyl,
(21) purinyl,
(22) carbazolyl,
(23) isoxazolyl,
(24) benzthiazolyl,
(25) benzoxazolyl
(26) thiazolyl, and
(27) oxazolyl.

One genus of this embodiment is the compounds wherein:
$R_1$ is substituted $C_{1-6}$alkyl, wherein the substituent is selected from the group consisting of:
(a) hydrogen,
(b) carboxy,
(c)

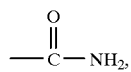

(d) $C_{6-10}$aryl or $C_{6-10}$aryl $C_{1-6}$alkyl wherein the aryl group is selected from the group consisting of
(1) phenyl,
(2) naphthyl,
(3) thienyl,
(4) imidazolyl,
(5) benzimidazolyl,
(6) pyrimidyl,
(7) benzofuryl,
(8) benzothienyl,
(9) indolyl,
and mono and di-substituted $C_{6-10}$aryl as defined above in items (1) to (9) wherein the substituents are independently selected from $C_{1-6}$alkyl, $C_{1-6}$alkyloxy, halo, hydroxy, amino, $C_{1-6}$alkylamino, and $C_{1-6}$alkylcarbonyl;

(e)

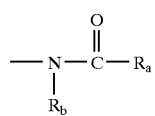

wherein $R_a$ and $R_b$ are each independently hydrogen, $C_{6-10}$ aryl wherein the aryl group is selected from the group consisting of
(1) phenyl,
(2) naphthyl,
(3) thienyl,
(4) imidazolyl,
(5) benzimidazolyl,
(6) pyrimidyl,
(7) benzofuryl,
(8) benzothienyl,
(9) indolyl,
and mono and di-substituted $C_{6-10}$ aryl as defined above; or substituted $C_{1-6}$alkyl wherein the substitutent is selected from hydroxy, halo, and benzyl, or wherein $R_a$ and $R_b$ are joined together to form a lactam or benzolactam ring as defined above.

One class of this genus is the compounds wherein:
$R_2$ is $CHR_cR_d$ wherein
$R_c$ is (a) H,
(b) $C_{1-3}$alkyl, or
(c) hydroxyl;
$R_d$ is
$C_{6-10}$aryl $C_{1-2}$alkyl or $C_{6-10}$aryl substituted $C_{1-2}$ alkyl, wherein the substituent is $C_{1-3}$alkyl or hydroxy, and wherein the aryl group is selected from the group consisting of
(1) phenyl,
(2) naphthyl,
(3) thienyl,
(4) imidazolyl,
(5) benzimidazolyl,
(6) pyrimidyl,
(7) benzofuryl,
(8) benzothienyl,
(9) indolyl,
and mono and di-substituted $C_{6-10}$aryl as defined above in items (1) to (9) wherein the substituents are independently selected from $C_{1-6}$alkyl, $C_{1-6}$alkyloxy, halo, hydroxy, and $C_{1-6}$alkylcarbonyl.

A sub-class of this class is the compounds wherein:
$R_3$ is
(a) H,
(b) $C_{1-10}$alkyl,
(c) phenyl, substituted phenyl, wherein the substitutent is carboxy, carboxy $C_{1-3}$alkyl, arnino carbonyl.

Within this sub-class are the compounds wherein:
AA is an amino acid including glycine, alanine, valine, leucine, isoleucine, serine, threonine, aspartic acid, asparagine, glutamic acid, glutamine, lysine, hydroxylysine, homohistidine, arginine, phenylalanine, tyrosine, tryptophan, cysteine, methionine, ornithine, homoserine, or citrulline.

Alternatively, within this sub-class the amino acids AA can be defined as follows:

AA is

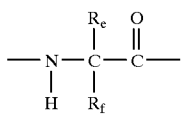

wherein $R_e$ and $R_f$ are individually selected from:
(a) hydrogen,
(b) $C_{1-4}$alkyl,
(c) mercapto $C_{1-3}$alkyl,
(d) hydroxy $C_{1-4}$alkyl,
(e) carboxy $C_{1-4}$alkyl,
(f) amino $C_{1-4}$alkyl,
(g) aminocarbonyl $C_{1-4}$alkyl,
(h) mono- or di-$C_{1-6}$alkyl amino $C_{1-4}$alkyl,
(i) guanidino $C_{1-4}$alkyl,
(j) substituted phenyl $C_{1-4}$alkyl, wherein the substituent is hydrogen, hydroxy, carboxy, or $C_{1-3}$ alkyl,
(k) substituted indolyl $C_{1-4}$ alkyl, wherein the substituent is hydrogen, hydroxy, carboxy, or $C_{1-3}$ alkyl,
(i) substituted imidazolyl $C_{2-6}$ alkyl wherein the substituent is hydrogen, hydroxy, carboxy, or $C_{1-4}$ alkyl.

One group of compounds may be further identified as that wherein X is

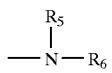

wherein $R_5$ and $R_6$ are each individually selected from the group consisting of
(a) H,
(b) $C_{1-10}$alkyl, or
(c) $C_{6-10}$aryl, or $C_{6-10}$aryl $C_{1-6}$alkyl wherein the aryl group is selected from the group consisting of
(1) phenyl,
(2) naphthyl,
(3) thienyl,
(4) imidazolyl,
(5) benzimidazolyl,
(6) pyrimidyl,
(7) benzofuryl,
(8) benzothienyl,
(9) indolyl, and
(10) pyridyl.

A smaller group within this group are the compounds wherein:
$R_d$ is $C_{1-4}$alkyl $C_{6-10}$aryl $C_{1-2}$alkyl,
$R_3$ is (a) H, or
(b) $C_{1-10}$alkyl; and
$R_1$ is $C_{6-10}$aryl $C_{1-6}$alkyl; and
$R_b$ is H.

Exemplifying the invention are the following compounds:
(a) N-[1(R)-Carboxy-ethyl]-α-(S)-(2-phenyl-ethyl) glycine-(L)-leucine, N-phenylamide;
(b) N-[1(R)-Carboxy-ethyl]-α-(S)-(2-phenyl-ethyl) glycine-(L)-isoleucine, N-phenylamide;
(c) N-[1(R)-Carboxy-ethyl]-α-(S)-(2-phenyl-ethyl) glycine-(L)-alanine, N-phenylamide;
(d) N-[1(R)-Carboxy-ethyl]-α-(S)-(2-phenyl-ethyl) glycine-(L)-phenylalanine, N-phenylamide;
(e) N-[1(R)-Carboxy-ethyl]-α-(S)-(2-phenyl-ethyl) glycine-(L)-serine-O-benzyl ether, N-phenylamide;
(f) N-[1(R)-Carboxy-ethyl]-α-(S)-(2-phenyl-ethyl) glycine-(L)-tryptophan, N-phenylamide;
(g) N-[1(R)-Carboxy-ethyl]-α-(S)-(2-phenyl-ethyl)] glycine-α-(S)-(2-phenyl-ethyl)glycine, N-phenylamide;
(h) N-[1(R)-Carboxy-ethyl]-α-(S)-(2-phenyl-ethyl) glycine-(L)-norleucine, N-phenylamide;
(i) N-[1(R)-Carboxy-ethyl]-α-(S)-(2-phenyl-ethyl) glycine-(L)-valine, N-phenylamide;
(j) N-[1(R)-Carboxy-ethyl]-α-(S)-(2-phenyl-ethyl) glycine-(L)-serine, N-phenylamide hydrochloride;
(k) N-[1(R)-Carboxy-ethyl]-α-(S)-(2-phenyl-ethyl) glycine-(L)-asparagine, N-phenylamide;
(l) N-[1(R)-Carboxy-ethyl]-α-(S)-(2-phenyl-ethyl) glycine-(L)-threonine, N-phenylamide hydrochloride;
(m) N-[1(R)-Carboxy-ethyl]-α-(S)-(2-phenyl-ethyl) glycine-(L)-lysine, N-phenylamide;
(n) N-[1(R)-Carboxy-ethyl)]-α-(S)-(2-phenyl-ethyl) glycine-(L)-glutamic acid, N-phenylamide;
(o) N-[1(R)-Carboxy-ethyl)]-α-(S)-(2-phenyl-ethyl) glycine-(L)-tyrosine, N-phenylamide hydrochloride;
(p) N-[1(R)-Carboxy-5-(1,3-dioxo-isoindolin-2-yl) pentyl]-α-(S)-(2-phenyl-ethyl)glycine-(L)-leucine, N-phenylamide;
(q) N-[1(R)-Carboxy-5-(1-oxo-isoindolin-2-yl)pentyl]-α-(S)-(2-phenyl-ethyl)glycine-(S)-leucine, N-phenylamide hydrochloride;
(r) N-[1(R)-Carboxy-5-(1-oxo-isoindolin-2-yl)pentyl]-α-(S)-(2-phenyl-ethyl)glycine-(S)-arginine, N-phenylamide;
(s) N-[1(R)-Carboxy-ethyl]-α-(S)-(2-(3-hydroxyphenyl)-ethyl)glycine-(S)-leucine, N-phenylamide hydrochloride;
(t) N-[1(R)-Carboxy-ethyl]-α-(S)-(2-(4-methylphenyl)-ethyl)glycine-(S)-leucine, N-phenylamide hydrochloride;
(u) N-[1(R)-Carboxy-ethyl]-α-(S)-(2-(2'-thienyl)ethyl) glycine-(L)-Leucine, N-phenylamide;
(v) N-(1 (R)-Carboxy-ethyl)-α-(S)-(2-(4-ethylphenyl) ethyl)glycine-(L)-leucine, N-phenylamide;
(w) N-[1(R)-Carboxy-5-(1-oxo-isoindolin-2-yl)pentyl]-α-(S)-(2-(4-propylphenyl)ethyl)glycine-(L)-leucine, N-phenylamide;
(x) N-(1 (R)-Carboxy-ethyl)-α-(S)-(2-(4-chlorophenyl) ethyl)glycine-(L)-leucine, N-phenylamide;
(y) N-[1(R)-Carboxy-ethyl)]-α-(S)-(2-phenyl-ethyl)] glycine-α-(S)-(2-cyclohexyl-ethyl)glycine, N-phenylamide;
(z) N-[1(R)-Carboxy-ethyl)]-α-(S)-(2-phenyl-ethyl)] glycine-α-(S)-(cyclohexyl)glycine, N-phenylamide;
(aa) N-[1(R)-Carboxy-ethyl)]-α-(S)-(2-phenyl-ethyl)] glycine-α-(S)-(cyclohexylmethyl)glycine, N-phenylamide;
(ab) N-[1(R)-Carboxy-ethyl)]-α-(S)-(2-phenyl-ethyl) glycine-(L)-β-naphthylalanine, N-phenylamide;
(ac) N-[1(R)-Carboxy-ethyl)]-α-(S)-(2-phenyl-ethyl) glycine-(L)-α-naphthylalanine, N-phenylamide;
(ad) N-[1(R)-Carboxy-ethyl)]-α-(S)-(2-phenyl-ethyl) glycine-[(L)-glutamic acid, α, δ-bis-N-phenylamide];
(ae) N-[1(R)-Carboxy-ethyl)]-α-(S)-(2-phenyl-ethyl) glycine-(L)-leucine, N-cyclohexylamide;

(ae) N-[(1 (R)-Carboxy-ethyl)]-α-(S)-(2-phenyl-ethyl) glycine-α-(S)-(4-hydroxyphenyl-ethyl)glycine, N-phenylamide;

(af) N-[1(R)-Carboxy-ethyl)]-α-(S)-(2-phenyl-ethyl) glycine-(L)-phenylglycine, N-phenylamide;

(ag) N-[1(R)-Carboxy-ethyl)]-α-(S)-(2-phenyl-ethyl) glycine-[(L)-glutamic acid, $N_\delta$-benzylamide, $N_\alpha$-phenylamide];

(ah) N-[1(R)-Carboxy-ethyl)]-α-(S)-(2-phenyl-ethyl) glycine-(L)-Ornithine, N-phenylamide;

(ai) N-[1(R)-Carboxy-ethyl)]α-(S)-(2-phenyl-ethyl) glycine-(L)-arginine, N-phenylamide;

(aj) N-[1(R)-Carboxy-ethyl)]-α-(S)-(2-phenyl-ethyl) glycine-α-(S)-(3-phenylpropyl)glycine, N-phenylamide;

(ak) N-[1(R)-Carboxy-ethyl)]-α-(S)-(2-phenyl-ethyl) glycine-α-(S)-n-octylglycine, N-phenylamide;

(al) N-[1(R)-Carboxy-ethyl]-α-(S)-(2-phenyl-ethyl) glycine-(L)-leucine, N-(4-carboxyphenyl)amide;

(am) N-[1(R)-Carboxy-ethyl]-α-(S)-(2-phenyl-ethyl) glycine-(L)-leucine, N-4-trifluoromethylphenyl)amide;

(an) N-[1(R)-Carboxy-ethyl]-α-(S)-(2-phenyl-ethyl) glycine-(L)-leucine, N-(3-pyridyl)amide;

(ao) N-[1(R)-Carboxy-ethyl]-α-(S)-(2-phenyl-ethyl) glycine-(L)-leucine, N-(benzothiazol-2-yl)amide;

(ap) N-[1(R)-Carboxy-ethyl]-α-(S)-(2-(4-n-propylphenyl)ethyl)glycine-(L)-leucine, N-phenylamide;

(aq) N-[1(R)-carboxy-ethyl]-α-(S)-(2-(4-propylphenyl) ethyl)glycine-(L)-Arginine, N-phenylamide;

(ar) N-[1(R)-Carboxy-ethyl]-α-(S)-(2-(3,4-dimethylphenyl-ethyl))glycine-(L)-leucine, N-phenylamide.

This invention also concerns pharmaceutical composition and methods of treatment of stromelysin-mediated or implicated disorders or diseases (as described above) in a patient (whcih shall be defined to include man and/or mammalian animals raised in the dairy, meat, or fur industries or as pets) in need of such treatment comprising administration of the stromelysin inhibitors of formula I as the active constituents.

Similarly, this invention also concerns pharmaceutical compositions and methods of treatment of collagenase mediated or implicated disorders or diseases (as described above) in a patient in need of such treatment comprising administration of the collagenase inhibitors of formula (I) as the active constituents.

Similarly, this invention also concerns pharmaceutical compositions and methods of treatment of gelatinase-mediated or implicated disorders or diseases (as described above) in a patient in need of such treatment comprising administration of the gelatinase inhibitors of formula (I) as the active constituents.

Moreover the invention also encompasses compositions, treatment, and method for co-administration of a compound of formula I with a PMN elastase inhibitor such as those described in EP 0 337 549 which published on Oct. 18, 1989, which is hereby incorporated by reference.

Compounds of the instant invention are conveniently prepared using the procedures described generally below and more explicitly described in the Example section thereafter.

SCHEME I-METHOD A

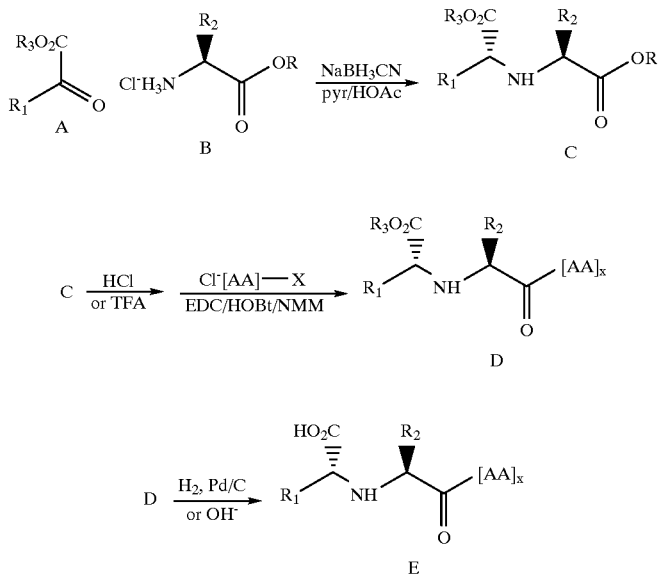

The reactions of Scheme I (Method A) involve the reductive amination of keto acid or ester derivative A with amino acid derivative B to form N-carboxylalkyl derivative C. The reaction is conveniently conducted in a mixture of pyridine and acetic acid with slow addition of sodium cyanoborohydride. The diastereomers of C are conveniently separated by column chromatography or HPLC. Reaction of diester C with hydrochloric acid followed by condensation with a substituted amino acid derivative [AA]-X results in Compound D. This reaction sequence advantageously employs the use of condensing agents such as dicyclohexylcarbodiimide (DDC) or water-soluble carbodiimide (N-ethyl-N'-(3-diethylaminopropyl)-carbodiimide; EDC). This reaction is also assisted by the formation of active ester intermediates such as those derived from 1-hydroxybenzotriazole, 4-nitrophenol, or 4-picolyl alcohol. The amino acid derivatives [AA]-X are prepared from appropriately protected N-protected amino acid derivatives condensed with X under similar conditions cited for the formation of D. $R_3$ may be removed by hydrogenolysis (when $R_3=CH_2$aryl) or by basic hydrolysis to give amino acid E.

SCHEME II-METHOD B

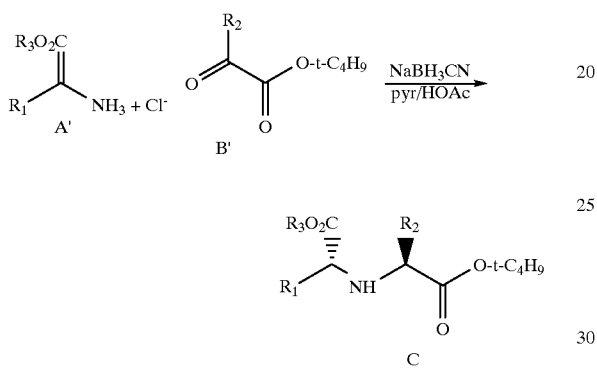

An alternative method is shown in Scheme II (Method B). In a reductive amination process similar to the one described for Method A, amino acid derivative A' is reacted with keto ester derivative B' to form N-carboxylalkyl derivative C. This diester C is then modified as in Method A.

SCHEME III-METHOD C

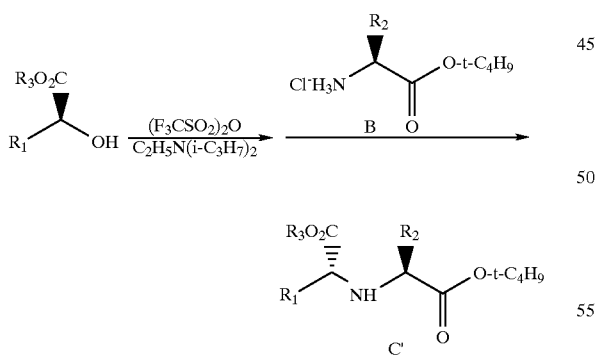

A second alternative is shown in Scheme III (Method C). In this variation an activated (S)-α-hydroxy ester is reacted with amino acid derivative B to form N-carboxyalkyl derivative C'. Compound C' is then reacted with [AA]-X as in Method A to form D.

SCHEME IV-Method D

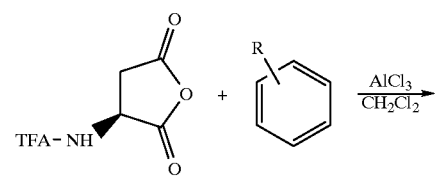

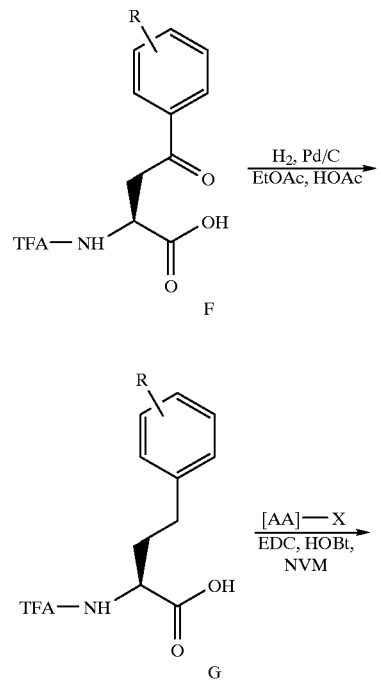

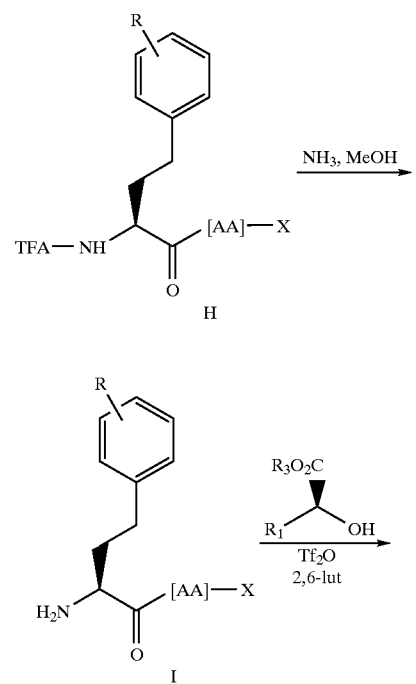

-continued

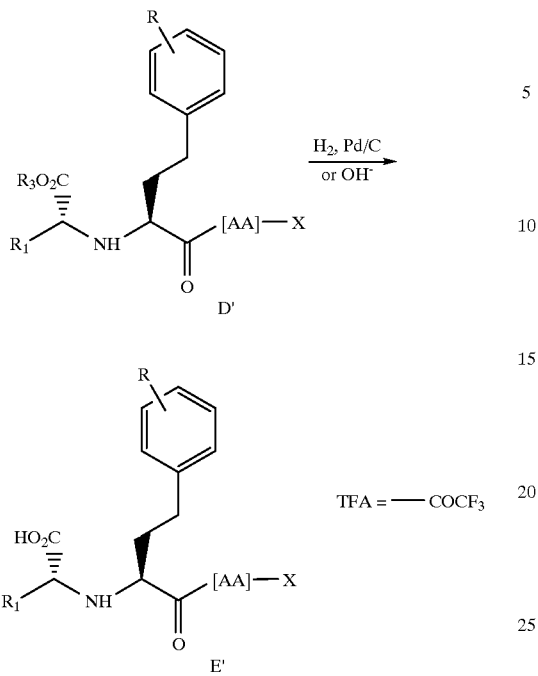

TFA = —COCF₃

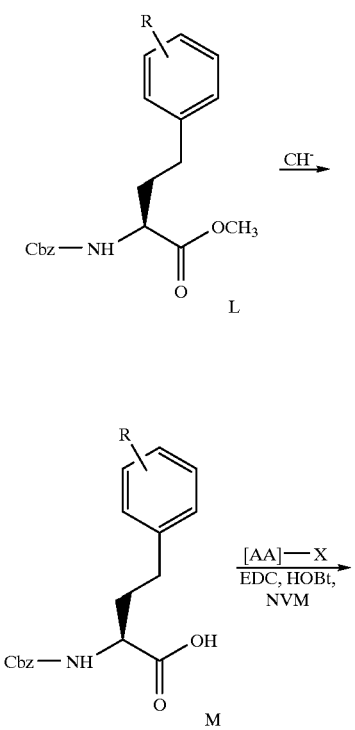

An alternative method involving the preparation of substituted phenylethyl amino acid is shown in Scheme IV (Method C). The Friedel-Crafts acylation of N-trifluoroacetyl-L-aspartic acid anhydride (prepared by the described method: M. Lapidus, M. Sweeney J. Med. Chem. 16, 163 (1973)) with a substituted benzene in the presence of aluminum chloride gave aroyl amino acid derivative F. The aryl ketone was reduced by catalytic hydrogenation to G. Condensation of G with amino acid [AA]-X by the procedure described in Method A gave N-trifluoroacetamide dipeptide H. Deprotection of H with ammonia in methanol gave the free amine I. Reaction with activated benzyl (L)-lactate by the procedure described in Method C gave N-carboxyethyl dipeptide benzyl ester D'. Catalytic hydrogenation as described in Method A gave the N-carboxyethyl dipeptide E'

SCHEME V-METHOD E

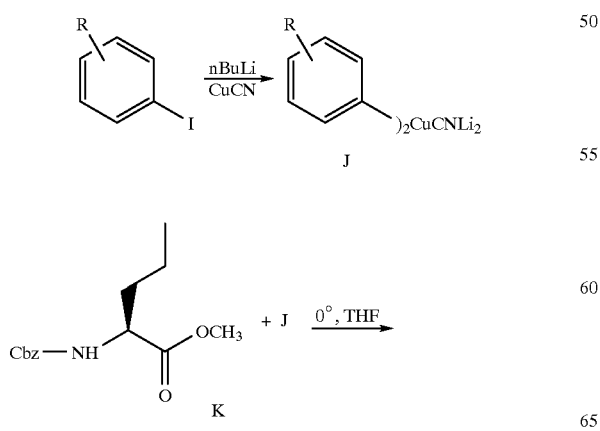

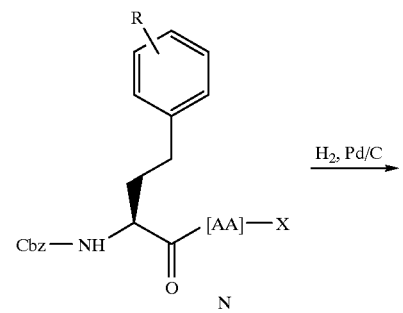

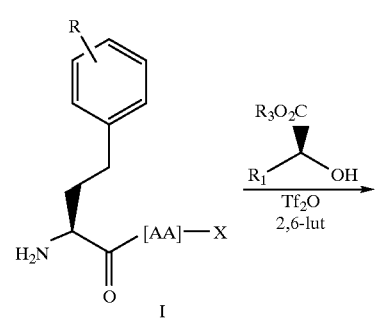

-continued

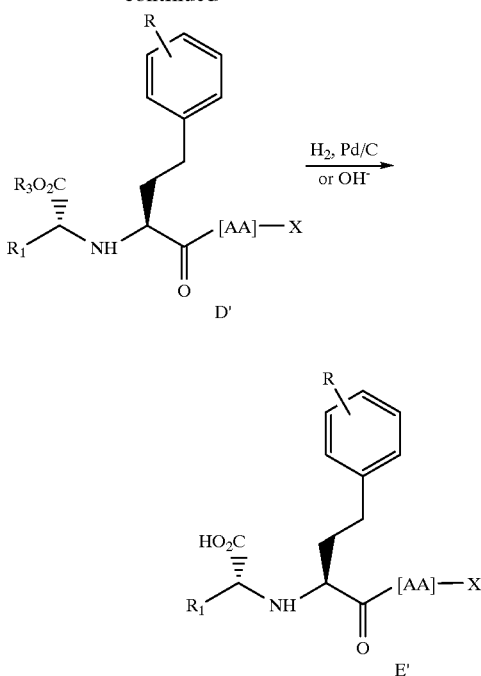

An alternative method for the preparation of substituted phenylethyl amino acids is shown in Scheme V (Method E). A substituted aryl iodide is lithiated with n-butyl lithium and reacted with copper(l) cyanide by the method of B. L Lipschutz, D. Parker, J. A. Kozlowski *J. Org. Chem.*, 48, 3334 (1983) to form the higher order cuprate complex J. Iodoethyl glycine derivative K was reacted with J to form phenethyl amino acid derivative L. Basic hydrolysis gave free acid M which is subsequently coupled with amino acid derivative [AA]-X by the procedure described in Method A to give N. Catalytic hydrogenation of N gave the free amine I which is subsequently modified to N-carboxyalkyl dipeptides D' and E' according to the procedure described in Method D.

A representative number of compounds of the instant invention of the formula (I) are shown below to exhibit in vitro inhibitory activities with respect to stromelysin, collagenase, and gelatinase. In particular, the compounds of formula (I) have been shown to inhibit the hydrolysis of substance P, SEQ ID NO:1 (that is, Arg-Pro-Lys-Pro-Gln-Gln-Phe-Phe-Gly-Leu-Met-$NH_2$) by stromelysin employing the method described in detail in the literature: R. Harrison, J. Teahan, R. Stein, "A semicontinuous, high-performance liquid chromatography-based assay for stromelysin", Analytical Biochem, 180, 110–113 (1989). Compounds of formula I were shown to inhibit the cleavage of a thioester containing peptide, Ac-Pro-Leu-Gly-"S-Leu"-Leu-Giy-$OC_2H_5$, by collagenase employing the previously described method: H. Weingarten, R. Martin, J. Feder, Biochem, 24, 6730–34 (1985). The peptide portion is herein designated SEQ ID No: 2:. Inhibition of gelatinase-mediated cleavage of the fluorogenic substrate Dnp-Pro-Leu-Gly-Leu-Trp-Ala-D-Arg$NH_2$ by compounds of Formula I were demonstrated employing the method of M. S. Stack and R. D. Gray, J. Biol. Chem. 264, 4277 (1989).

TABLE 1

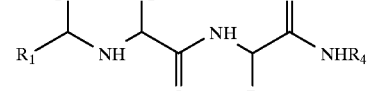

| | $R_1$ | $R_2$ | $R_3$ | $NHR_4$ | Inhibition of Stromelysin pH = 7.5 ($IC_{50}$, μM) | Inhibition of Collagenase pH = 6.5 ($IC_{50}$, μM) | Inhibition of 72 kD Galatinase pH = 7.5 ($K_i$, μM) |
|---|---|---|---|---|---|---|---|
| 5a | $CH_3$ | (S)—$(CH_2)_2$Ph | (S)-i-$C_4H_9$ | NHPh | 0.32 | 0.06 | 0.93 |
| 5b | $(CH_2)_3$Ph | $(CH_2)_2$Ph | (S)-i-$C_4H_9$ | NHPh | 0.78 | 2.6 | 2.1 |
| 5c | $(CH_2)_4$Ph | (S)—$(CH_2)_2$Ph | (S)-i-$C_4H_9$ | NHPh | 0.50 | 0.07 | |
| 5d | (R)—$(CH_2)_4$Phth | $(CH_2)_2$Ph | (S)-i-$C_4H_9$ | NHPh | 0.20 | 0.25 | 0.086 |
| 5e | (R)—$(CH_2)_4$Phth | $(CH_2)_3$Ph | (S)-i-$C_4H_9$ | NHPh | 0.19 | 1.4 | |
| 5f | (R)—$(CH_2)_4$Phth | $(CH_2)_2$Ph | (S)-i-$C_4H_9$ | $NHCH_3$ | 0.25 | 0.18 | |
| 5g | (R)—$(CH_2)_4$Phth | $(CH_2)_2$Ph | (S)—$(CH_2)_4NH_3Cl$ | $NHCH_3$ | 1.1 | 0.36 | |
| 5h | (R)—$(CH_2)_4$Phth | $(CH_2)_2$Ph | (S)-i-$C_4H_9$ | (S)—Phe$NH_2$ | 0.20 | 4.0 | |
| 5i | (R)—$(CH_2)_4$N—FMOC | $(CH_2)_2$Ph | (S)-i-$C_4H_9$ | NHPh | 1.4 | 1.7 | | where Phth = phthalimido: 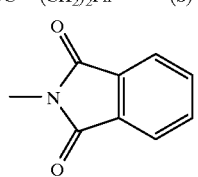 and FMOC = fluorenylmethyloxycarbonyl: 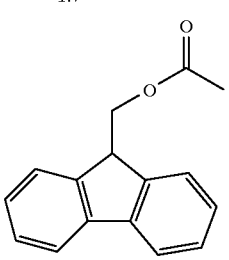

The remainder of the compounds in Table 1 have an $IC_{50}$ or $K_i$ of 4.0 μM or less for stromelysin TABLE 1-continued

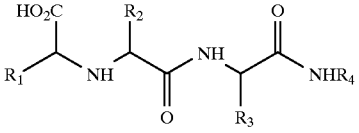

| | $R_1$ | $R_2$ | $R_3$ | $NHR_4$ |
|---|---|---|---|---|
| 5j | (R)—$CH_3$ | $(CH_2)_2Ph$ | (S)-i-$C_4H_9$ | NH-n-$C_4H_9$ |
| 5k | (R)—$CH_3$ | $(CH_2)_3Ph$ | (S)-i-$C_4H_9$ | NHPh |
| 5l | (R)—$CH_3$ | $(CH_2)_2$-Naph | (S)-i-$C_4H_9$ | NHPh |
| 5m | (R)—$CH_3$ | $(CH_2)_2$-β-Naph | (S)-i-$C_4H_9$ | NHPh |
| 5n | $CH_3$ | (S)-$CH_2$-3-indolyl | (S)-i-$C_4H_9$ | NHPh |
| 5o | $C_2H_5$ | (S)—$(CH_2)_2Ph$ | (S)-i-$C_4H_9$ | NHPh |
| 5p | n-$C_4H_9$ | (S)—$(CH_2)_2Ph$ | (S)-i-$C_4H_9$ | NHPh |
| 5q | n-$C_6H_{13}$ | (S)—$(CH_2)_2Ph$ | (S)-i-$C_4H_9$ | NHPh |
| 5r | n-$C_{10}H_{21}$ | (S)—$(CH_2)_2Ph$ | (S)-i-$C_4H_9$ | NHPh |
| 5s | n-$C_{12}H_{25}$ | (S)—$(CH_2)_2Ph$ | (S)-i-$C_4H_9$ | NHPh |
| 5t | n-$C_{14}H_{29}$ | (S)—$(CH_2)_2Ph$ | (S)-i-$C_4H_9$ | NHPh |
| 5u | (R)—$CH_3$ | $(CH_2)_2$-2-furyl | (S)-i-$C_4H_9$ | NHPh |
| 5v | (R)—$CH_3$ | $(CH_2)_2$-2-thienyl | (S)-i-$C_4H_9$ | NHPh |
| 5w | $CH_3$ | (S)—$(CH_2)_2Ph$ | (S)-s-$C_4H_9$ | NHPh |
| 5x | $CH_3$ | (S)—$(CH_2)_2Ph$ | (S)—$CH_3$ | NHPh |
| 5y | $CH_3$ | (S)—$(CH_2)_2Ph$ | (S)—$CH_2Ph$ | NHPh |
| 5z | $CH_3$ | (S)—$(CH_2)_2Ph$ | (S)—$(CH_2)_2$—O—$CH_2Ph$ | NHPh |
| 5aa | $CH_3$ | (S)—$(CH_2)_2Ph$ | (S)—$CH_2CONH_2$ | NHPh |
| 5ab | $CH_3$ | (S)—$(CH_2)_2Ph$ | (S)—CH—((S)—OH)$CH_3$ | NHPh |
| 5ac | $CH_3$ | (S)—$(CH_2)_2Ph$ | (S)—$(CH_2)$-3-indolyl | NHPh |
| 5ad | $CH_3$ | (S)—$(CH_2)_2Ph$ | (S)—$(CH_2)_2Ph$ | NHPh |
| 5ae | $CH_3$ | (S)—$(CH_2)_2Ph$ | (S)—$(CH_2)_4NH_2$ | NHPh |
| 5af | $CH_3$ | (S)—$(CH_2)_2Ph$ | (S)—$(CH_2)_9NH_2$ | NHPh |
| 5ag | $CH_3$ | (S)—$(CH_2)_2Ph$ | (S)—$(CH_2)_3N(CH_3)_2$ | NHPh |
| 5ah | $CH_3$ | (S)—$(CH_2)_2Ph$ | (S)—$(CH_2)_3$N-3-quinuclidinyl | NHPh |
| 5ai | $CH_3$ | (S)—$(CH_2)_2Ph$ | (S)—$(CH_2)_2$CO-4-morpholinyl | NHPh |
| 5aj | $CH_3$ | (S)—$(CH_2)_2Ph$ | (S)—$(CH_2)_3$-4-morpholinyl | NHPh |
| 5ak | $CH_3$ | (S)—$(CH_2)_2Ph$ | (S)—$(CH_2)_2CO_2H$ | NHPh |
| 5al | $CH_3$ | (S)—$(CH_2)_2Ph$ | (S)—$CH_2Ph$-4-OH | NHPh |
| 5am | $CH_3$ | (S)—$(CH_2)_2Ph$ | (S)-n-$C_4H_9$ | NHPh |
| 5an | $CH_3$ | (S)—$(CH_2)_2Ph$ | (S)-i-$C_3H_7$ | NHPh |
| 5ao | $CH_3$ | (S)—$(CH_2)_2Ph$ | (S)—$CH_2OH$ | NHPh |
| 5ap | $CH_3$ | (S)—$(CH_2)_2Ph$ | (S)—$C_2H_4$-cyclo-$C_6H_{11}$ | NHPh |
| 5aq | $CH_3$ | (S)—$(CH_2)_2Ph$ | (S)-cyclo-$C_6H_{11}$ | NHPh |
| 5ar | $CH_3$ | (S)—$(CH_2)_2Ph$ | (S)—$CH_2$-cyclo-$C_6H_{11}$ | NHPh |
| 5as | $CH_3$ | (S)—$(CH_2)_2Ph$ | (S)—$CH_2$-β-Naphthyl | NHPh |
| 5at | $CH_3$ | (S)—$(CH_2)_2Ph$ | (S)—$CH_2$-α-Naphthyl | NHPh |
| 5au | $CH_3$ | (S)—$(CH_2)_2Ph$ | (S)—$(CH_2)_2$CONHPh | NHPh |
| 5av | $CH_3$ | (S)—$(CH_2)_2Ph$ | (S)-i-$C_4H_9$ | NH-cyclo-$C_6H_{11}$ |
| 5aw | $CH_3$ | (S)—$(CH_2)_2Ph$ | (S)—$(CH_2)_2Ph$-4-OH | NHPh |
| 5ax | $CH_3$ | (S)—$(CH_2)_2Ph$ | (S)—Ph | NHPh |
| 5ay | $CH_3$ | (S)—$(CH_2)_2Ph$ | (S)—$(CH_2)_2$CONH$CH_2Ph$ | NHPh |
| 5az | $CH_3$ | (S)—$(CH_2)_2Ph$ | (S)—$(CH_2)_3NH_2$ | NHPh |
| 5ba | $CH_3$ | CH$(CH_3)CH_2Ph$ | (S)-i-$C_4H_9$ | NHPh |
| 5bb | $CH_3$ | (S)—$(CH_2)_2Ph$ | (S)—$(CH_2)_3Ph$ | NHPh |
| 5bc | $CH_3$ | (S)—$(CH_2)_2Ph$ | (S)—$(CH_2)_3$NHC(NH)$NH_2$ | NHPh |
| 5bd | (R)—$CH_3$ | $(CH_2)_2Ph$-3-$CH_3$ | (S)-i-$C_4H_9$ | NHPh |
| 5be | (R)—$CH_3$ | $(CH_2)_2Ph$-4-$CH_3$ | (S)-i-$C_4H_9$ | NHPh |
| 5bf | (R)—$CH_3$ | $(CH_2)_2Ph$-4-$OCH_3$ | (S)-i-$C_4H_9$ | NHPh |
| 5bg | (R)—$CH_3$ | $(CH_2)_2Ph$-4-$OC_2H_5$ | (S)-i-$C_4H_9$ | NHPh |
| 5bh | (R)—$CH_3$ | $(CH_2)_2Ph$-4-OH | (S)-i-$C_4H_9$ | NHPh |
| 5bi | (R)—$CH_3$ | $(CH_2)_2Ph$-3-OH | (S)-i-$C_4H_9$ | NHPh |
| 5bj | (R)—$CH_3$ | $(CH_2)_2Ph$-4-$C_2H_5$ | (S)-i-$C_4H_9$ | NHPh |
| 5bk | (R)—$CH_3$ | $(CH_2)_2Ph$-4-n-$C_3H_7$ | (S)-i-$C_4H_9$ | NHPh |
| 5bl | (R)—$CH_3$ | $(CH_2)_2Ph$-4-i-$C_3H_7$ | (S)-i-$C_4H_9$ | NHPh |
| 5bm | (R)—$CH_3$ | $(CH_2)_2Ph$-3-Cl | (S)-i-$C_4H_9$ | NHPh |
| 5bn | (R)—$CH_3$ | $(CH_2)_2Ph$-4-Cl | (S)-i-$C_4H_9$ | NHPh |
| 5bo | (R)—$CH_3$ | $(CH_2)_2Ph$-4-F | (S)-i-$C_4H_9$ | NHPh |
| 5bp | (R)—$CH_3$ | $(CH_2)_2Ph$-4-$CF_3$ | (S)-i-$C_4H_9$ | NHPh |
| 5bq | (R)—$CH_3$ | $(CH_2)_2Ph$-3,4-$(CH_3)_2$ | (S)-i-$C_4H_9$ | NHPh |
| 5br | (R)—$(CH_2)_4$NHCO$CH_3$ | $(CH_2)_2Ph$ | (S)-i-$C_4H_9$ | NHPh |
| 5bs | (R)—$(CH_2)_4$-(1-$H_2$)—Phth | $(CH_2)_2Ph$ | (S)-i-$C_4H_9$ | NHPh |
| 5bt | (R)—$(CH_2)_4$-(1-$H_2$)—Phth | $(CH_2)_2Ph$ | (S)—$(CH_2)_3$NHC(NH)$NH_2$ | NHPh |
| 5bu | (R)—$(CH_2)_4$-(1-$H_2$)—Phth | $(CH_2)_2Ph$-4-n-$C_3H_7$ | (S)-i-$C_4H_9$ | NHPh |
| 5bv | (R)—$CH_3$ | $(CH_2)_2Ph$-4-n-$C_3H_7$ | (S)—$(CH_2)_3$NHC(NH)$NH_2$ | NHPh |
| 5bw | (R)—$(CH_2)_4$-(1-$H_2$)—Phth | $(CH_2)_2Ph$-4-n-$C_3H_7$ | (S)—$(CH_2)_3$NHC(NH)$NH_2$ | NHPh |
| 5bx | (R)—$(CH_2)_4$-(1-$H_2$)—Phth | $(CH_2)_2Ph$-4-n-$C_3H_7$ | (S)-i-$C_4H_9$ | NH$CH_3$ |
| 5by | (R)—$(CH_2)_4$-(1-$H_2$)—Phth | $(CH_2)_2Ph$-4-n-$C_3H_7$ | (S)—$(CH_2)_3$NHC(NH)$NH_2$ | NH$CH_3$ |
| 5bz | (R)—$(CH_2)_4$NHCOPh | $(CH_2)_2Ph$ | (S)-i-$C_4H_9$ | NHPh |

TABLE 1-continued

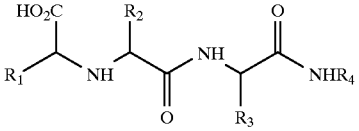

| | R₁ | R₂ | R₃ | NHR₄ |
|---|---|---|---|---|
| 5ca | (R)—(CH₂)₄NHCOCH₂Ph | (CH₂)₂Ph | (S)-i-C₄H₉ | NHPh |
| 5cb | (R)—(CH₂)₄NHCO(CH₂)₂Ph | (CH₂)₂Ph | (S)-i-C₄H₉ | NHPh |
| 5cc | (R)—(CH₂)₄NHCOPh | (CH₂)₂Ph | (S)—CH₂Ph | NHPh |
| 5cd | (R)—(CH₂)₄NHCOCH₂Ph | (CH₂)₂Ph | (S)—CH₂Ph | NHPh |
| 5ce | (R)—(CH₂)₄NHCO(CH₂)₂Ph | (CH₂)₂Ph | (S)—CH₂Ph | NHPh |
| 5cf | (R)—(CH₂)₄NHCO(CH₂)₃Ph | (CH₂)₂Ph | (S)—CH₂Ph | NHPh |
| 5cg | (R)—(CH₂)₄NHCO-cyclo-C₆H₁₁ | (CH₂)₂Ph | (S)—CH₂Ph | NHPh |
| 5ch | (R)—(CH₂)₄NHCO(CH2)₂-cyclo-C₆H₁₁ | (CH₂)₂Ph | (S)—CH₂Ph | NHPh |
| 5ci | (R)—(CH₂)₄NHCO(CH₂)₃-cyclo-C₆H₁₁ | (CH₂)₂Ph | (S)—CH₂Ph | NHPh |
| 5cj | (R)—(CH₂)₄NHCOCH₂-cyclo-C₆H₁₁ | (CH₂)₂Ph | (S)—CH₂Ph | NHPh |
| 5ck | (R)—(CH₂)₃NH₂ | (CH₂)₂Ph | (S)-i-C₄H₉ | NHPh |
| 5cl | (R)—(CH₂)₃NHCO-Pro-Ac | (CH₂)₂Ph | (S)-i-C₄H₉ | NHPh |
| 5cm | (R)—(CH₂)₃NHCOPh | (CH₂)₂Ph | (S)-i-C₄H₉ | NHPh | where (1-H₂)-Phth =

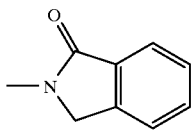

| 5cn | (R)—CH₃ | (S)—(CH₂)₂Ph | (S)-i-C₄H₉ | NHCH(CH₃)Ph |
|---|---|---|---|---|
| 5co | (R)—CH₃ | (S)—(CH₂)₂Ph | (S)-i-C₄H₉ | NHPh-4-CO₂CH₃ |
| 5cp | (R)—CH₃ | (S)—(CH₂)₂Ph | (S)-i-C₄H₉ | NHPh-4-CO₂H |
| 5cq | (R)—CH₃ | (S)—(CH₂)₂Ph | (S)-i-C₄H₉ | NHPh-3-CO₂CH₃ |
| 5cr | (R)—CH₃ | (S)—(CH₂)₂Ph | (S)-i-C₄H₉ | NHPh-3-CO₂H |
| 5cs | (R)—CH₃ | (S)—(CH₂)₂Ph | (S)-i-C₄H₉ | NHPh-4-OCH₃ |
| 5ct | (R)—CH₃ | (S)—(CH₂)₂Ph | (S)-i-C₄H₉ | NHPh-3-OCH₃ |
| 5cu | (R)—CH₃ | (S)—(CH₂)₂Ph | (S)-i-C₄H₉ | NHPh-4-OH |
| 5cv | (R)—CH₃ | (S)—(CH₂)₂Ph | (S)-i-C₄H₉ | NHPh-4-CF₃ |
| 5cw | (R)—CH₃ | (S)—(CH₂)₂Ph | (S)-i-C₄H₉ | NHPh-3-CF₃ |
| 5cx | (R)—CH₃ | (S)—(CH₂)₂Ph | (S)-i-C₄H₉ | NH-2-pyridinyl |
| 5cy | (R)—CH₃ | (S)—(CH₂)₂Ph | (S)-i-C₄H₉ | NH-3-pyridinyl |
| 5cz | (R)—CH₃ | (S)—(CH₂)₂Ph | (S)-i-C₄H₉ | NH-4-pyridinyl |
| 5da | (R)—CH₃ | (S)—(CH₂)₂Ph | (S)-i-C₄H₉ | NH-4-pyrimidinyl |
| 5db | (R)—CH₃ | (S)—(CH₂)₂Ph | (S)-i-C₄H₉ | NH-2-benzthiazolyl |
| 5dc | (R)—CH₃ | (S)—(CH₂)₂Ph | (S)-i-C₄H₉ | NH-2-benzimidazolyl |
| 5dd | (R)—CH₃ | (S)—(CH₂)₂Ph | (S)-i-C₄H₉ | NH-(5-methyl-3-isoxazolyl) |
| 5de | (R)—CH₃ | (S)—(CH₂)₂Ph | (S)-n-C₈H₁₇ | NHPh |
| 5df | (R)—(CH₂)₄NH₃⁺Cl⁻ | (CH₂)₂Ph | (S)-i-C₄H₉ | NHPh |
| 5dg | (R)—CH₃ | (S)—(CH₂)₂Ph-4-i-C₄H₉ | (S)-i-C₄H₉ | NHPh |
| 5dg | (R)—CH₃ | (S)—(CH₂)₂Ph-4-n-C₄H₉ | (S)-i-C₄H₉ | NHPh |

This invention also relates to a method of treatment for patients (including man and/or mammalian animals raised in the dairy, meat, or fur industries or as pets) suffering from disorders or diseases which can be attributed to stromelysin as previously described, and more specifically, a method of treatment involving the administration of the matrix metalloendoproteinase inhibitors of formula (I) as the active constituents.

Accordingly, the compounds of formula (I) can be used among other things in the treatment of osteoarthritis and rheumatoid arthritis, and in diseases and indications resulting from the over-expression of these matrix metalloendoproteinases such as found in certain metastatic tumor cell lines.

For the treatment of rheumatoid arthritis, osteoarthritis, and in diseases and indications resulting from the overexpression of matrix metalloendoproteinases such as found in certain metastatic tumor cell lines or other diseases mediated by the matrix metalloendoproteinases, the compounds of formula (I) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of Formula (I) are employed. (For purposes of this application, topical application shall include mouth washes and gargles.)

Dosage levels of the order of from about 0.05 mg to about 140 mg per kilogram of body weight per day are useful in the treatment of the above-indicated conditions (about 2.5 mg to about 7 gms. per patient per day). For example, inflammation may be effectively treated by the administration of from about 0.01 to 50 mg of the compound per kilogram of body weight per day (about 0.5 mg to about 3.5 gms per patient per day).

The amount of active ingredient that may be combined with the carrier materials to produce a single dosage form will vary depending upon the host treated and the particular mode of administration. For example, a formulation intended for the oral administration of humans may contain from 0.5 mg to 5 gm of active agent compounded with an appropriate and convenient amount of carrier material which may vary from about 5 to about 95 percent of the total composition. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following Examples are intended to illustrate the preparation of compounds of Formula I, and as such are not intended to limit the invention as set forth in the claims appended, thereto.

EXAMPLE 1

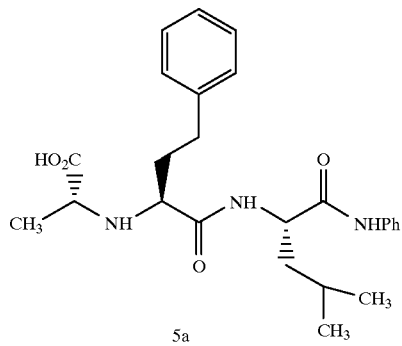

Employing the procedure outlined in Scheme 1, Method A, compound number 5a was prepared as follows:

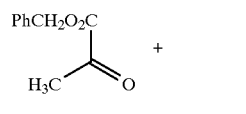

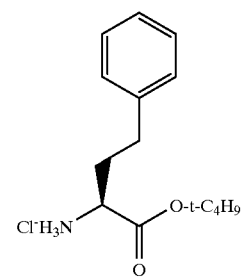

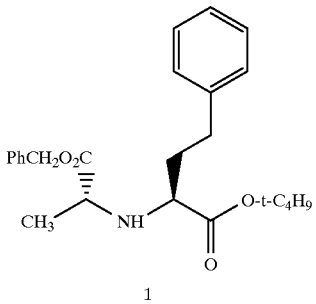

N-[1(R)-Benzyloxycarbonyl-ethyl)]-α-(S)-(2-phenyl-ethyl) glycine, t-butyl ester (1)

To a solution of 10.5 g of (S)-α-(2-phenyl-ethyl)glycine, t-butyl ester in 50 mL each of acetic acid and pyridine at 0° C. was added 27.2 mL of a 1.0M solution of sodium cyanoborohydride (NaBH$_3$CN) in tetrahydrofuran (THF) followed by 18.1 mL of benzyl pyruvate. Additional NaH$_3$BCN (50 mL, 1.0M) was then added over 5 hours via syringe pump. The mixture was allowed to warm slowly to ambient temperature during the first 30 minutes of this addition. The reaction mixture was then poured into a slurry of ice and 100 mL of concentrated hydrochloric acid (HCl) and extracted with 500 mL of 30% ether/hexane (discarded).

The aqueous slurry (containing the desired HCl salt) was then extracted three times with ethyl acetate and the combined organic layers were washed three times with saturated aqueous sodium bicarbonate. The mixture was dried over anhydrous sodium sulfate and concentrated in vacuo to give 20 g of a yellow oil. The mixture was purified by flash column chromatography on silica-gel (120×200 mm column, 10% ethyl acetate/hexane) to give 6.40 g of a colorless oil: R$_f$=0.25 (10% ethyl acetate/hexane): $^1$H NMR (200 MHz, CD$_3$OD) δ7.13–7.37 (m, 10H), 5.12 (ABq, 2H, J=5.1 Hz), 3.36 (q, 1H, J=7.0 Hz), 3.15 (t, 1H, J=6.4 Hz), 2.65 (m, 2H), 1.90 (m, 2H), 1.45 (s, 9H), 1.26 (d, 3H, J=7.0 Hz).

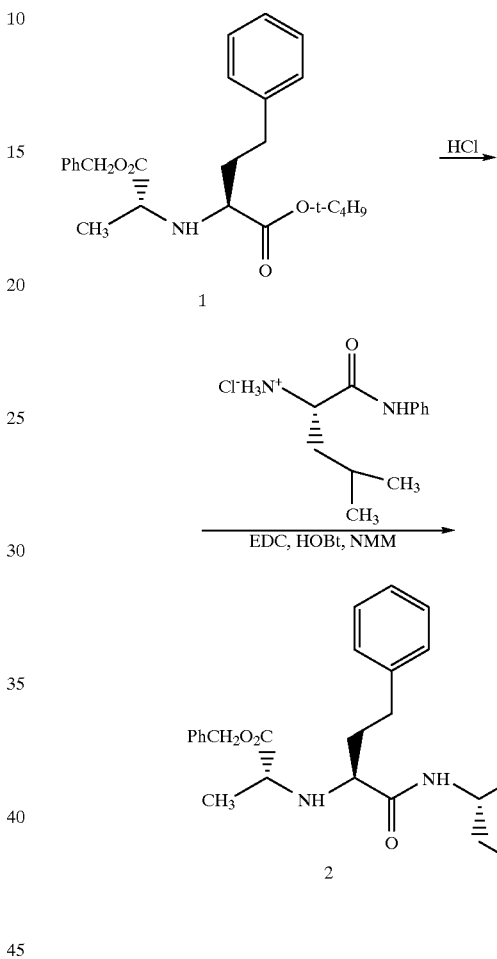

N-[1(R)-Benzyloxycarbonyl-ethyl)]-α-(S)-(2-phenethyl) glycine-(L)-leucine, N-phenylamide (2)

N-[1(R)-Benzyloxycarbonyl-ethyl)]-α-(S)-(2-phenethyl) glycine, t-butyl ester (1) (6.40 g) was dissolved in a small amount of ethyl acetate and 250 mL of a saturated solution of anhydrous HCl in ethyl acetate was added. The mixture was held for 7 hours at 50° C. then cooled and concentrated in. vacuo to give a colorless solid which was used without further purification: $^1$H NMR (200 MHz, CD$_3$OD) δ7.41–7.20 (m, 10H), 5.25 (AB, 2H, J=12.1 Hz), 4.27 (q, 1H, J=7.3 Hz), 4.06 (t, 1H, J=6.6 Hz), 2.9–2.7 (m, 2H), 2.24 (m, 2H), 1.55 (d, 3H, J=7.4 Hz).

The crude aminoacid hydrochloride, (L)-Leucine, N-phenylamide hydrochloride (3.71 g, 18.0 mmol), and hydroxybenzotriazole (3.31 g, 24.5 mmol) were dissolved in 250 mL of dimethylformamide (DMF). N-methyl morpholine (NMM) (3.6 mL, 32.7 mmol) was added and the mixture cooled to 0° C. Ethyl dimethylaminopropyl carbodiimide (EDAC, 3.76 g, 19.6 mmol) was added and the mixture stirred for 16 hours at ambient temperature. The solution was diluted with 1 L of ethyl acetate and washed three times with saturated aqueous sodium bicarbonate and three times with water. The mixture was then dried over anhydrous sodium sulfate and concentrated in vacuo to give a pale yellow oil. The product was purified by MPLC (35×350 mm column, 30% ethyl acetatelhexane) to afford 8.31 g of the desired peptide as a colorless glass:

$^1$H NMR (200 MHz, CD$_3$OD) δ7.57–7.08 (m, 15H), 5.13 (ABq, 2H, J=5 Hz), 4.57 (m, 1H), 3.47 (q, 1H, J=7.1 Hz), 3.25 (t, 1H, J=6.4 Hz), 2.67 (t, 2H, J=8.1 Hz), 2.1–1.6 (m, 5H), 1.31 (d, 3H, J=7.0 Hz), 0.98 (d, 3H, J=6.5 Hz), 0.96 (d, 3H, J=6.0 Hz).

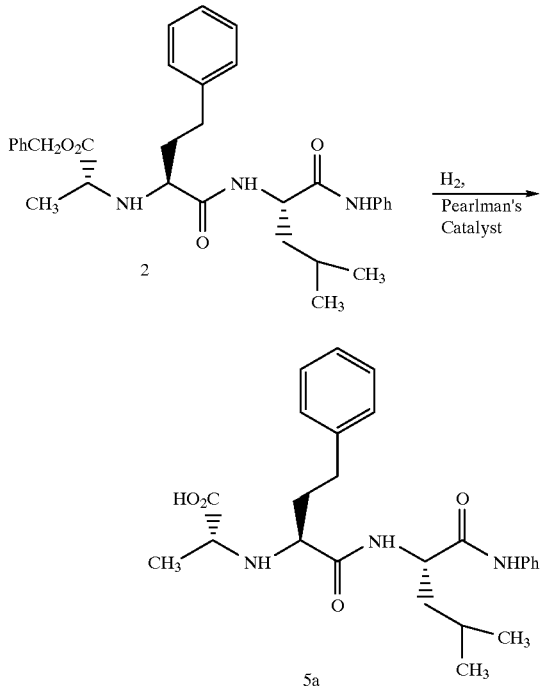

N-[1(R)-Carboxy-ethyl]-α-(S)-(2-phenyl-ethyl)glycine-(L)-leucine, N-phenylamide (5a)

To a solution of 8.31 g of N-[1(R)-benzyloxycarbonyl-ethyl)]-α-(S)-(2-phenethyl)glycine-(L)-leucine, N-phenylamide (2) in 125 mL of methanol was added 500 mg of Pearlman's catalyst. After 3 hours of vigorous stirring under an atmosphere of hydrogen, the mixture was filtered through Celite filter aid and concentrated in vacuo to give 6.50 g of amino acid 5a as a colorless solid: $^1$H NMR (200 MHz, CH$_3$OD) δ7.59–7.08 (m, 10H), 4.65 (m, 1H), 3.96 (t, 1H, J=6.8 Hz), 3.58 (q, 1H, J=7.4 Hz), 2.9–2.6 (m, 2H), 2.15 (m, 2H), 1.52 (d, 3H, J=7.4 Hz), 1.02 (d, 3H, J=6.0 Hz), 1.00 (d, 3H, J=6.0 Hz).

The following additional compounds were prepared according to the method of Example 1.

N-[1(R)-Carboxy-ethyl]-α-(S)-(2-phenyl-ethylglycine-(L)-isoleucine, N-phenylamide (5w)

MS: mle 440 (M$^+$) $^1$H NMR (CD$_3$OD, 200 MHz): δ7.56 (dd, 2H, J=8.0, 2.0 Hz), 7.34–7.09 (m, 8H), 4.42 (d, 1H, J=8.0 Hz), 4.01 (t, 1H, J=6.0 Hz), 3.58 (q, 1H, J=7.0 Hz), 2.68 (m, 2H), 2.14 (m, 2H), 1.64 (m, 1H), 1.48 (d, 3H, 7.0 Hz), 1.30 (m, 2H), 1.03 (d, 3H, J=6.5 Hz), 0.96 (t, 3H, J=7.0 Hz).

N-[1(R)-Carboxy-ethyl)]-α-(S)-(2-phenyl-ethyl)glycine-(L)-alanine, N-phenylamide (5x)

MS: m/e 398 (M$^+$) $^1$H NMR (CD30D,200 MHz): δ7.56 (dd, 2H, J=8.0, 2.0 Hz), 7.33–7.19 (m, 8H), 4.56 (q, 1H, J=7.0 Hz,), 3.95 (t, 1H, J=6 Hz), 3.60 (q, 1H, J=7.0 Hz), 2.75 (m, 2H), 2.17 (m, 2H) 1.48 (d, 6H, J=7.0 Hz).

N-[1(R)-Carboxy-ethyl)]-α-(S)-(2-phenyl-ethyl)glycine-(L)-phenylalanine, N-phenylamide (5y)

MS: m/e 474 (M$^+$) $^1$H NMR (CD$_3$OD,200 MHz): δ7.51 (dd, 2H, J=8.0, 2 Hz), 7.32–7.09 (m, 13H), 4.93 (dd, 1H, J=9.0, 6.0 Hz), 3.90 (t, 1H, J=6.0 Hz), 3.40 (q, 1H, J=7.0 Hz), 3.26 (dd, 1H, J=4.0, 13 Hz), 3.01 (dd,1H, J=9.0, 13 Hz), 2.68 (t, 2H, J=8.0 Hz), 2.12 (dd, 2H, J=6.0, 9.0 Hz), 1.29 (d, 3H, J=7.0 Hz).

N-[1(R)-Carboxy-ethyl)]-α-(S)-(2-phenyl-ethyl)glycine-(L)-serine-O-benzyl ether. N-phenylamide (5z)

MS: m/e 504 (M$^+$) $^1$H NMR (CD$_3$OD,200 MHz): δ7.55 (dd, 2H, J=8.0, 2.0 Hz), 7.34–7.10 (m, 13H, ArH), 4.60 ppm (s, 1H), 4.58 (s, 1H), 4.04 (t, 1H, J=6 Hz), 3.84 (d, 2H, J=6.0 Hz), 3.75 (q, 1H, J=7.0 Hz), 2.74 (dd, 2H, J=6.0, 2.0 Hz), 2.18 (t, 2H, J=7.0 Hz), 1.49 (d, 3H, J=9.0 Hz).

N[1(R)-Carboxy-ethyl)]-α-(S)-(2-phenyl-ethyl)glycine-(L)-tryptophan, N-phenylamide (5ac)

MS: m/e 513 (M$^+$) $^1$H NMR (CD30D, 200 MHz): δ7.65 (dd, 1H, J=7.0, 2.0 Hz), 7.47 (dd, 2H, J=8.0, 1.0 Hz), 7.30–6.99 (m, 12H), 4.94 (dd, 1H, J=9.0, 7.0 Hz), 3.82 (t, 1H, J=6.0 Hz), 3.34 (dd, 2H, J=4.0, 9.0 Hz), 3.27 (q, 1H, J=6.0 Hz), 2.64 (m, 2H), 2.10 (td, 2H, J=8.0, 2.0 Hz), 1.23 (d, 3H, J=7.0 Hz).

N[1(R)-Carboxy-ethyl)]-α-(S)-(2-phenyl-ethyl)]glycine-α-(S)-(2-phenyl-ethyl)glycine, N-phenylamide (5ad)

MS: m/e 488 (M$^+$) $^1$H NMR (CD$_3$OD, 200 MHz): δ7.56 (dd, 2H, J=8.0, 1.0 Hz), 7.33–7.08 (m, 13H,), 4.58 (dd, 1H, J=9.0, 7.0 Hz), 4.02 (t, 1H, J=6.0 Hz), 3.64 (q, 1H, J=7.0 Hz), 2.74 (m, 4H), 2.16 (m, 4H), 1.51 (d, 3H, J=7.0 Hz).

N-[1(R)-Carboxy-ethyl)]-α-(S)-(2-phenyl-ethyl)glycine-(L)-norleucine, N-phenylamide (5am)

MS: m/e 440 (M$^+$) $^1$H NMR (CD$_3$OD, 200 MHz): δ7.56 (dd, 2H, J=8.0, 1.0 Hz), 7.33–7.08 (m, 8H), 4.52 (dd, 1H, J=8.0, 6.0 Hz), 3.98 (t, 1H, J=6.0 Hz), 3.59 (q, 1H, J=7.0 Hz), 2.71 (m, 2H), 2.16 (t, 2H, J=8.0 Hz), 1.85 (m, 2H), 1.48 ppm (d, 3H, J=7.0 Hz), 1.43 (m, 4H), 0.94 (t, 3H, J=7.0 Hz).

N[1(R)-Carboxy-ethyl)]-α-(S)-(2-phenyl-ethyl)glycine-(L)-valine, N-phenylamide (5an)

MS: m/e 426 (M$^+$) $^1$H NMR (CD$_3$OD, 200 MHz): δ7.56 (dd, 2H, J=8.0, 1.0 Hz), 7.33–7.09 (m, 8H), 4.37 (d, 1H, J=8.0 Hz), 4.04 (t, 1H, J=7.0 Hz,), 3.60 (q, 1H, J=7.0 Hz), 2.68 (m, 2H), 2.16 (m, 3H), 1.49 (d, 3H, J=7.0 Hz), 1.06 (d, 6H, J=7 Hz).

N-[1(R)-Carboxy-ethyl)]-α-(S)-(2-phenyl-ethyl)glycine-(L)-serine, N-phenylamide Hydrochloride (5ao)

MS: m/e 414 (M$^+$) $^1$H NMR (CD$_3$OD, 200 MHz): δ7.57 (dd, 2H, J=8.0, 1.0 Hz), 7.34–7.09 (m, 8H), 4.68 (t, 1H, J=8.0 Hz), 3.88 (d, 2H, J=6.0 Hz), 3.51 (t, 1H, J=8.0 Hz), 3.10 (q, 1H, J=7.0 Hz), 2.78 (m, 2H,), 2.24 (m, 2H), 1.60 (d, 3H, J=7.0 Hz).

N[1(R)-Carboxy-ethyl)]-α-(S)-(2-phenyl-ethyl)glycine-(L)-asparagine, N-phenylamide (5aa)

MS: m/e 441 (M$^+$) 1H NMR (CD$_3$OD, 200 MHz): δ7.57 (dd, 2H, J=2.0, 8.0 Hz), 7.14–7.34 (m, 8H), 4.86 (d, 1H, J=7.0 Hz), 3.92 (t, 1H, J=6.0 Hz), 3.64 (q, 1H, J=7 Hz), 2.6–2.8 (m, 2H), 2.1–2.25 (m, 4H), 1.47 (d, 3H, J=7.0 Hz).

N[1(R)-carboxy-ethyl)]-α-(S)-(2-phenyl-ethyl)glycine-(L)-threonine, N-phenylamide hydrochloride (5ab)

MS: m/e 428 (M$^+$) $^1$H NMR (CD$_3$OD,200 MHz): δ7.66 (d, 2H, J=8.0 Hz), 7.12–7.34 (m, 8H), 4.56 (d, 1H, J=5.0 Hz), 4.1–4.3 (m, 2H), 4.09 (q, 1H, J=7.0 Hz), 2.7–2.8 (m, 2H), 2.2–2.3 (m, 2H), 1.63 (d, 3H, J=7.0 Hz), 1.32 (d, 3H, J=6.0 Hz),.

N-[1(R)-Carboxy-ethyl)]-α-(S)-(2-phenyl-ethyl)glycine-(L)-lysine, N-phenylamide (5ae)

MS: m/e 455 (M$^+$) $^1$H NMR (CD$_3$OD, 200 MHz): δ7.57 (dd, 2H, J=2.0, 8.0 Hz), 7.04–7.29 (m, 8H), 4.55 (dd, 1H,

J=5.0, 10.0 Hz), 3.26 (t, 1H, J=7.0 Hz), 3.19 (t, 1H, J=7.0 Hz), 2.95 (t, 1H, J=7.0 Hz), 2.69 (t, 2H, J=8.0 Hz), 1.85–2.0 (br. m, 4H), 1.60, 1.70 (2m, 4H), 1.30 (d, 3H, J=7 Hz).

N-[1(R)-Carboxy-ethyl)]-α-(S)-(2-phenyl-ethyl)glycine-(L)-glutamic acid, N-phenylamide (5ak)

MS: m/e 456 (M+) $^1$H NMR (CD$_3$OD, 200 MHz): δ7.57 (dd, 2H, J=2.0, 8.0 Hz), 7.12–7.33 (m, 8H), 4.67 (dd, 1H, J=6.0, 9.0 Hz), 4.02 (t, 1H, J=6.0 Hz), 3.66 (q, 1H, J=7.0 Hz), 2.67–2.74 (t, 2H, J=7.0 Hz), 2.46–2.54 (m, 2H), 2.1–2.23 (br. m, 4H), 1.51 (d, 3H, J=7.0 Hz). Combustion Analysis C$_{24}$H$_{29}$N$_3$O$_6$ (0.20 H$_2$O) Calc: C, 62.79, H. 6.45, N, 9.15 Found: C, 62.79, H, 6.50, N. 9.15

N-[1(R)-Carboxy-ethyl)]-α-(S)-(2-phenyl-ethyl)glycine-(L)-tyrosine, N-phenylamide hydrochloride (5al)

MS: m/e 490 (M+–HCl) $^1$H NMR (CD$_3$OD, 200 MHz): δ7.53 (dd, 2H, J=2.0, 8.0 Hz), 7.10–7.33 (m, 8H), 6.74 (dd, 2H, J=2.0, 8.0 Hz), 4.89 (dd, 1H, J=6.0, 9.0 Hz), 3.99 (t, 1H, J=6.0 Hz), 3.59 (q, 1H, J=7.0 Hz), 3.24 (dd, 1H, J=8.0, 15.0 Hz)1, 2.93 (dd, 1H, J=10.0, 15.0 Hz), 2.67–2.76 (t, 2H, J=7.0 Hz), 2.10–2.23 (br. m, 2H), 1.46 (d, 3H, J=7.0 Hz).

EXAMPLE 2

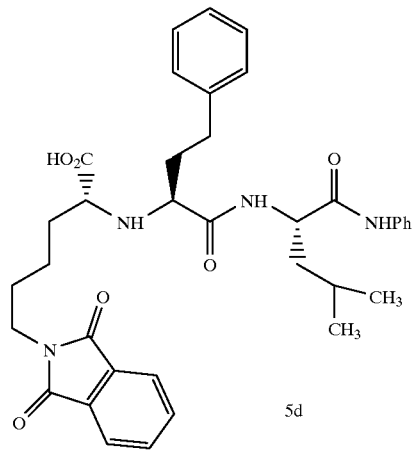

Employing the procedure outlined in Method B, N-[1(R)-Benzyloxycarbonyl-5-(1,3-dioxo-isoindolinyl-2-yl)pentyl]-α-(S)-(2-phenyl-ethyl)glycine, t-butyl ester 4 was prepared and converted to compound 5d using methodology described in Method A for aminodipeptide 2 and aminoacid 5a.

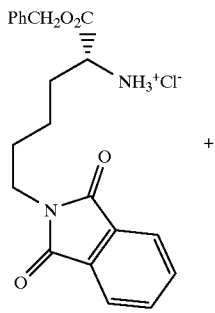

+

N-[1 (R)-Benzyloxycarbonyl-5-(1,3-dioxo-isoindolin-2-yl) pentyl]-α-(S)-(2-phenyl-ethyl)glycine, t-butyl ester (4)

To a solution of E-phthalimido (D)-Lysine benzyl ester hydrochloride (1.23 g, 3.05 mmol) in 2.5 mL each of acetic acid and pyridine at 0° C. was added 0.5 mL of a 1.0M solution of NaH$_3$BCN in THF followed by t-butyl 2-oxo-4-phenylbutanoate (1.43 g, 6.11 mmol). Additional NaH$_3$BCN (3.58 mL, 1.0M) in THF was then added over 3.5 hours via syringe pump. The mixture was allowed to warm slowly to ambient temperature during the first 30 minutes of this addition. The reaction mixture was poured into a slurry of ice and 15 mL of conc. HCl and extracted three times with ethyl acetate. The combined organic layers were washed three times with saturated aqueous sodium bicarbonate, dried over anhydrous sodium sulfate, and concentrated in vacuo. The mixture was purified by MPLC (35×300 mm column, 10–20% ethyl acetate/hexane by linear gradient) to give 801 mg of the desired amino ester as a colorless oil:

$^1$H NMR (CD$_3$OD, 200 MHz) δ7.82–7.71 (m, 4H), 7.35–7.08 (m, 10H), 5.09 (ABq, 2H, J=11.9 Hz), 3.61 (t, 2H, J=6.5 Hz), 3.21 (t, 1H, J=6.0 Hz), 3.06 (t, 1H, J=7.2 Hz), 2.60 (t, 2H, J=6.7 Hz), 2.0–1.3 (m, 8H), 1.42 (s, 9H).

Substituted α-keto-esters were also conveniently prepared by one of the following procedures:

t-Butyl 2-Oxo-5-phenylpentanoate

To a suspension of magnesium turnings (1.22 g, 50.23 mmol) in 20 mL of ether was added 1-bromo-3-phenylpropane (7.64 mL, 50.23 mmol) at a rate so as to maintain a gentle reflux. After the addition was complete, the mixture was stirred an additional 30 min. Di-tert-butyl oxylate (10.16 g, 50.23 mmol) was dissolved in 250 mL of ether and cooled to −780° C. The Grignard reagent was added dropwise so as to maintain an internal temperature ≤−75° C. The mixture was stirred for an additional hour at −78° C., and poured into a mixture of ice, 300 mL of 1N hydrochloric acid and 200 mL of ether. The mixture was shaken vigorously and the layers were separated. The ether layer was washed with water and saturated sodium chloride solution, then dried over magnesium sulfate, filtered, and concentrated to give 15.2 g of the title compound as a colorless oil: ¹H NMR (200 MHz, CDCl₃) δ7.36–7.04 (M, 5H), 2.79 (t, 2H), 2.67 (t, 2H), 1.97 (m, 2H), 1.57 (s, 9H).

t-Butyl 2-oxo-4-(4-methylphenyl)-butanoate

To a solution of 4-methylbenzaldehyde (2.5 mL, 21.2 mmol) in 25 mL of benzene was added 1 mL each of acetic acid and piperidine. The mixture was heated to reflux with azeotropic removal of water via a Dean-Stark trap. A solution of t-butyl pyruvate (3.36 g, 23.32 mmol) in 5 mL of benzene was added over 7 h by syringe pump. The mixture was cooled, diluted with ethyl acetate and washed three times with saturated aqueous sodium bicarbonate and three times with 1N hydrochloric acid. The organics were dried over sodium sulfate, filtered, and concentrated. The crude product was purified by MPLC on silica-gel eluting with 2.5% ethyl acetate in hexane to give the desired product as a yellow oil: ¹H NMR (200 MHz, CDCl₃) δ7.75 (d, 1H, J=16.19 Hz), 7.49 (d, 2H, J=8.25 Hz), 7.24 (m, 3H), 2.37 (s, 3H), 1.58 (s, 9H). The above product was dissolved in ethyl acetate and held under hydrogen in the presence of 100 mg of 10% palladium on carbon for 2 hours. The mixture was filtered and concentrated in vacuo to give 1.196 g of the title compound as a pale-yellow oil: ¹H NMR (200 MHz, CDCl₃) δ7.1–6.9 (m, 4H), 3.12 (t, 2H, J=6.8 Hz), 2.90 (t, 2H, J=7.3 Hz), 1.56 (s, 9H).

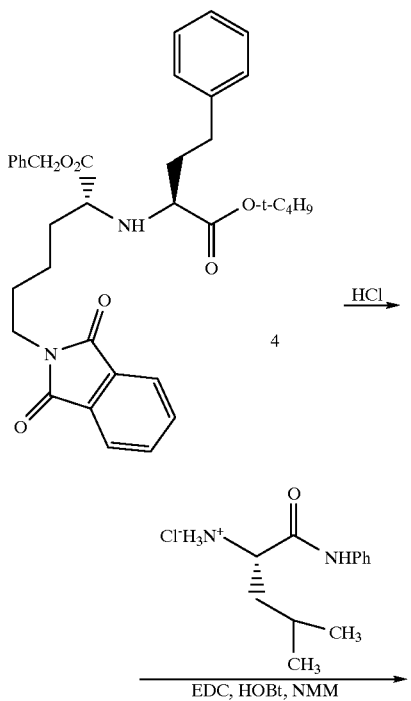

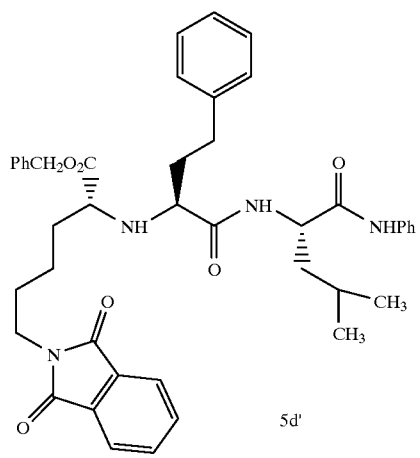

N-[1(R)-Benzyloxycarbonyl-5-(1,3-dioxo-isoindolin-2-yl)pentyl]-α-(S)-(2-phenyl-ethyl)]glycine-(L)-leucine, N-phenylamide (5d')

N-[1(R)-Benzyloxycarbonyl-5-(1,3-dioxo-isoindolin-2-yl)pentyl]-α-(S)-(2-phenyl-ethyl)glycine, t-butyl ester 4 (210 mg) was dissolved in a small amount of ethyl acetate and 15 mL of a saturated solution of anhydrous HCl in ethyl acetate was added. The mixture was held for 4 hours at 50° C. then cooled and concentrated in vacuo to give a colorless solid which was used without purification. The crude amino acid hydrochloride, (L)-Leucine, N-phenylamide hydrochloride (96 mg, 0.39 mmol), and hydroxybenzotriazole (97 mg, 0.72 mmol) were dissolved in 5 mL of DMF. N-methyl morpholine (165 ml, 32.7 mmol) was added and the mixture cooled to 0° C. Ethyl dimethylaminopropyl carbodiimide (EDAC, 104 mg, 0.54 mmol) was added and the mixture stirred for 16 hours at ambient temperature. The solution was diluted with ethyl acetate and washed three times with saturated aqueous sodium bicarbonate and three times with water. The mixture was dried over anhydrous sodium sulfate, concentrated in vacuo, and purified by MPLC (22× 300 mm column, 30% ethyl acetate/hexane) to afford 254 mg of the desired peptide as a colorless glass which crystallized upon standing:

¹H NMR (CD₃OD, 200 MHz) δ7.82–7.06 (m, 19H), 5.08 (ABq, 2H, J=12.5 Hz), 4.54 (t, 1H, J=6.3 Hz), 3.61 (t, 2H, J=6.6 Hz), 3.35 (t, 1H, J=6.0 Hz), 3.19 (dd, 1H, J=5.7, 6.9 Hz), 2.64 (m, 2H), 2.1–1.3 (m, 11H), 0.95 (d, 3H, J=6.4 Hz), 0.94 (d, 3H, J=6.42).

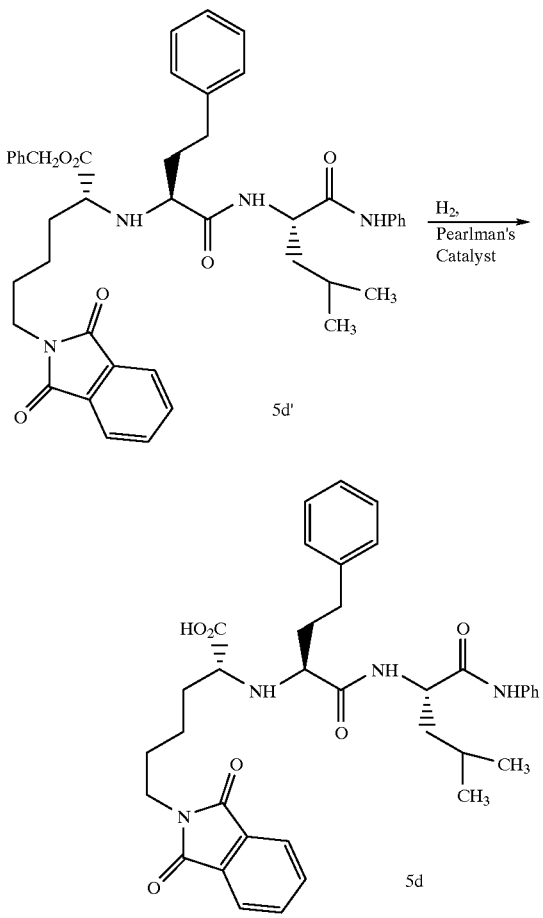

N-[1 (R)-Carboxy-5-(1,3-dioxo-isoindolin-2-yl)pentyl]-α-(S)-(2-phenyl-ethyl])glycine-(L)-leucine, N-phenylamide (5d)

To a solution of 254 mg of [N-[1(R)-benzyloxycarbonyl-5-(1,3-dioxo-isoindolin-2-yl)pentyl-α-(S)-(2-phenylethyl)] glycine-(L)-Leucine, N-phenylamide (5d') in 10 mL of methanol was added 10 mg of Pearlman's catalyst. After 1 hour of vigorous stirring under an atmosphere of hydrogen, the mixture was filtered through Celite filter aid and concentrated in vacuo to give 220 mg of [N-[1(R)-carboxy-4-(1,3-dioxo-2-isoindolin-2-yl)pentyl-α-(S)-[2-phenylethyl]] glycine-(L)-Leucine, N-phenylamide 5d as a colorless solid:

$^1$H NMR (CD$_3$OD, 200 MHz) δ7.85–7.08 (m, 14H), 4.62 (m, 1H), 3.81 (t, 1H, J=7.1 Hz), 3.69 (t, 2H, J=6.6 Hz), 3.48 (t, 1H, J=6.2 Hz), 2.8–2.6 (m, 2H), 2.3–1.4 (m, 11H), 0.98 (d, 6H, J=4.8 Hz).

The following additional compounds were prepared according to the method of Example 2.

N-[1(R)-Carboxy-5-(1-oxo-isoindolin-2-yl)pentyl]-α-(S)-(2-phenyl-ethyl)glycine-(L)-leucine, N-phenylamide hydrochloride (5bs)

MS: m/e 613 (M+1) $^1$H NMR (200 MHz, CD$_3$OD) δ7.81–7.09 (m, 14H), 4.66 (m, 1H), 4.53 (s, 2H), 4.09 (dd, 1H, J=5.24, 8.86 Hz), 3.94 (t, 1H, J=6.10 Hz), 3.8–3.5 (m, 2H), 2.9–2.6 (m, 2H), 2.3–1.3 (m, 9H), 0.99 (d, 3H, J=5.93 Hz), 0.98 (d, 3H, J 6.03 Hz).

N-[1(R)-Carboxy-5-(1-oxo-isoindolin-2-yl)pentyl]-α-(S)-(2-phenyl-ethyl?glycine-(L)-arginine, N-phenylamide (5bt)

MS: m/e 656 (M+1) $^1$H NMR (200 MHz, CD$_3$OD) δ7.76–7.0 (m, 14H), 4.66 (m, 1H), 4.48 (s, 2H), 3.63 (t, 2H, J=7.69 Hz), 3.15–3.08 (m, 4H), 2.63 (t, 2H, J=6.25 Hz), 2.1–1.4 (m, 13H).

N-[1(R)-Carboxy-ethyl]-α-(S)-(2-(3-hydroxyphenyl)-ethyl) glycine-(L)-leucine, N-phenylamide hydrochloride (5bi)

MS: m/e 456 (M+1) $^1$H NMR (200 MHz, CD$_3$OD) S 7.56 (dd, 2H, J=1.17, 8.33 Hz), 7.30 (t, 2H, J=7.69 Hz), 7.2–7.0 (m, 3H), 6.7–6.6 (m, 2H), 4.7–4.6 (m, 1H), 4.15–4.0 (m, 2H), 2.8–2.55 (m, 2H), 2.3–2.1 (m, 2H), 1.9–1.6 (m, 3H), 1.58 (d, 3H, J=7.30 Hz), 1.03 (d, 3H, J=6.06 Hz), 1.01 (d, 3H, 5.96 Hz).

N-[1 (R)-Carboxy-ethyl]-α-(S)-(2-(4-meihylphenyl)-ethyl) glyoine-(L)-leucine, N-phenylamide hydrochloride (5be)

MS: m/e 454 (M+1) $^1$H NMR (200 MHz, CD3OD) δ7.57 (dd, 2H, J=1.90, 8.99 Hz), 7.30 (t, 2H, J=7.26 Hz), 7.15–7.10 (m, 1H), 7.05 (s, 4H), 4.75–4.65 (m, 1H), 4.15–4.0 (m, 2H), 2.8–2.55 (m, 2H), 2.3–2.1 (m, 2H), 2.26 (s, 3H), 1.9–1.65 (m, 3H), 1.58 (d, 3H, J=7.68 Hz), 1.03 (d, 3H, J=6.04 Hz), 1.01 (d, 3H, 5.96 Hz).

N-[1(R)-Carboxy-ethyl]-α-(S)-(2-(2'-thienyl)ethyl)glycine-(L)-leucine, N-phenylamide (5v)

MS: m/e 446 (M$^+$); 468 (M+Na); 484 (M+K). $^1$H NMR (CD$_3$OD, 200 MHz): δ7.62–6.88 (m, 8H); 4.69 (dd, 1H); 4.10 (t, 1H); 3.98 (q, 1H); 3.04 (m, 2H); 2.30 (m, 2H); 1.78 (m, 3H); 1.62 (d, 3H); 1.08 (2d, 6H).

N-[1(R)-Carboxy-ethyl]-α-(S)-(2-(4-ethylphenyl)ethyl) glycine-(L)-leucine, N-phenylamide (5bi)

MS: m/e 468 (M+1) $^1$ H NMR (CD$_3$OD, 400 MHz): δ7.57 (d, 2H, J=8 Hz), 7.30 (t, 2H, J=8 Hz), 7.12–7.04 (m, 5H), 4.66(dd, 1H, J=9, 5 Hz), 4.10–4.02 (m, 2H), 2.73 (td, 1H, J=12, 6 Hz), 2.64 (td, 1H, J=12, 6 Hz), 2.57 (q, 2H, J=7 Hz), 2.24–2.08 (m, 2H), 1.82–1.63 (m, 3H), 1.59(d, 3H, J=7 Hz), 1.18 (t, 3H, J=7 Hz), 1.03 (d, 3H, J=6 Hz), 1.00 (d, 3H, J=6 Hz).

N[1(R)-Carboxy-5-(1-oxo-isoindolin-2-yl)pentyl]-α-(S)-(2-(4-propylphenyl)ethyl)lycine-(L)-Leucine, N-phenylamide (5bu)

MS: m/e 655 (M+1) $^1$H NMR (CD$_3$OD, 400 MHz): δ7.76 (d, 1H, J=7 Hz), 7.61–7.53 (m, 4H), 7.47 (t, 1H, J=7 Hz), 7.29 (t, 2H, J=8 Hz), 7.08 (t, 1H, J=7.5 Hz), 7.04 (d, 2H, J=7 Hz), 7.01 (d, 2H, J=7 Hz), 4.62(dd, 1H, J=9, 5 Hz), 4.51(s, 2H), 3.86 (dd, 1H, J=7, 5 Hz), 3.74–3.56 (m, 2H), 3.50 (t, 1H, J=6 Hz), 2.74–2.56 (m, 2H), 2.50 (t, 2H, J=7.5 Hz), 2.16–1.40 (m, 11H), 1.58 (hextet, 2H, J=7 Hz), 0.98 (d, 6H, J=6 Hz), 0.90 (t, 3H, J=7 Hz).

N-(1 (R)-Carboxy-ethyl)-α-(S)-(2-(4-chlorophenyl)ethyl) glycine-(L)-leucine, N-phenylamide (5bn)

MS: m/e 474 (M+1) $^1$H NMR (CD$_3$OD, 200 MHz): δ7.55 (d, 2H, J=8Hz), 7.29 (t, 2H, J=8 Hz), 7.22 (d, 2H, J=8 Hz), 7.16 (d, 2H, J=8 Hz), 7.09 (t, 1H, J=8 Hz), 4.65 (dd, 1H, J=8, 5 Hz), 4.06–3.96 (m, 2H), 2.88–2.56 (m, 2H), 2.30–2.04 (m, 2H), 1.84–1.46 (m, 3H), 1.58 (d, 3H, J=7 Hz), 1.02 (bd, 6H, J=7 Hz).

EXAMPLE 3

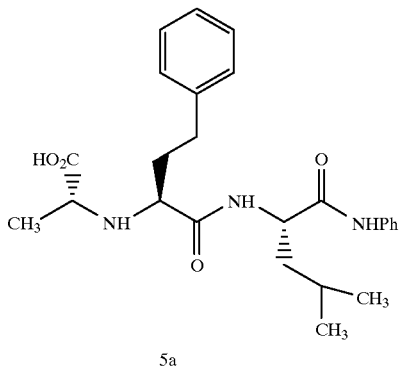

5a

Employing the procedure outlined in Method C, amino acid ester 1 was prepared as a single diastereomer and converted to compound 5a using methodology described in Example 1.

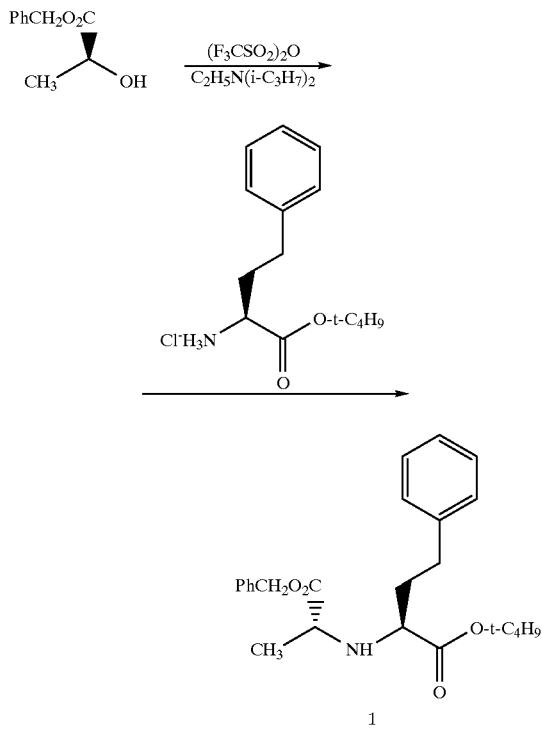

1

N[1(R)-Benzyloxycarbonyl-ethyl]-α-(S)-(2-phenyl-ethyl) glycine, t-butyl ester (1)

To a solution of benzyl (S)-lactate (3.75 g, 20.8 mmol) in dry methylene chloride (75 mL) cooled to 0° C. was added trifluoromethanesulfonic anhydride (3.75 mL, 22.3 mmol) dropwise over 5 minutes with stirring under an inert atmosphere. After 5 minutes at 0° C., 2,6-lutidine (2.77 mL, 23.8 mmol) was added in one portion. After stirring 10 minutes, at 0° C., N,N-diisopropylethylamine (4.0 mL, 23.0 mmol) was added followed immediately by a solution of (L)-homophenylalanine t-butyl ester (4.97 g, 21.1 mmol) in methylene chloride (40 mL) dropwise over 15 minutes with stirring. The cooling bath was then removed, and the mixture was stirred for 24 hours at room temperature. The mixture was diluted with methylene chloride (150 mL) which was successively washed with water, saturated aqueous sodium bicarbonate solution, saturated salt solution, dried over anhydrous magnesium sulfate and rotoevaporated. Purification was achieved by means of flash column chromatography on silica gel using initially 5% ethyl acetate in hexane and subsequently 10% ethyl acetate in hexane as the mobile phase. The product was obtained as an oil; yield 6.90 g (83%) and converted to 5a by the methodology described in Example 1.

The following examples were prepared from intermediates described in Example 3.

N[1(R)-Carboxy-ethyl)]-α-(S)-(2-phenyl-ethyl)]glycine-α-(S)-(2-cyclohexyl-ethyl)glycine, N-phenylamide (5ap)

MS: m/e 494 (M$^+$) $^1$H NMR (CD$_3$OD, 200 MHz): δ7.56 (dd, 2H, J=7.0, 1.0 Hz), 7.34–7.10 (m, 8H), 4.51 (dd, 1H, J=8.0, 6.0 Hz), 4.19 (m, 1H), 2.71 (m, 2H), 2.19 (m, 2H), 1.96–1.60 (m, aliphatic H's), 1.56 (dd, 3H, J=7.0, 3.0 Hz), 1.39–1.18 (m, aliphatic H's), 1.00–0.88 (m, aliphatic H's).

N-[1(R)-Carboxy-ethyl]-α-(S)-(2-phenyl-ethyl)]glycine-α-(S)-cyclohexyl-glycine, N-phenylamide (5ag)

MS: m/e 466 (M$^+$) $^1$H NMR (CD$_3$OD, 200 MHz): δ7.57 (dd, 2H, J=7.0, 1.0 Hz), 7.30–7.16 (m, 8H), 4.23–4.05 (m, 2H), 3.99 (d, 1H, J=1.0 Hz, 2.67 (m, 2H), 2.40–2.05 (m, 2H), 1.90–1.62 (m, aliphatic H's), 1.57 (d, 3H, J=7.0 Hz), 1.4–1.19 (m, aliphatic H's).

N-[1(R)-Carboxy-ethyl]-α-(S)-(2-phenyl-ethyl)glycine-α-(S)-cyclohexylmethyl-glycine, N-phenylamide (5ar)

MS: m/e 480 (M$^+$) $^1$H NMR (CD$_3$OD, 200 MHz): δ7.56 (dd, 2H, J=7.0, 1.0 Hz), 7.33–7.08 (m, 8H), 4.67 (t, 1H, J=8.0 Hz), 3.99 (t, 1H, J=7.0 Hz), 3.63 (q, 1H, J=7.0 Hz), 2.69 (m, 2H), 2.16 (m, 2H), 1.81 (m, 2H), 1.74 (m, 8H), 1.49 (d, 3H, J=7.0 Hz), 1.23 (td, J=7.0, 2.0 Hz), 1.02 (m, 2H).

N-[1(R)-Carboxy-ethyl)]-α-(S)-(2-phenyl-ethyl)glycine-(L)-β-naphthylalanine, N-phenylamide (5as)

MS: m/e 524 (M$^+$) $^1$H NMR (CD$_3$OD, 200 MHz): δ7.82–7.07 (m, 17H), 5.00 (dd, 1H, J=8.0, 6.0 Hz), 3.85 (t, 1H, J=7.0 Hz), 3.42 (dd, 1H, J=14.0, 6.0 Hz), 3.33 (q, 1H, J 7.0 Hz), 3.20 (dd, 1H, J=14.0, 9.0 Hz), 2.65 (t, 2H, J=9.0 Hz), 2.09 (t, 2H, J=8.0 Hz), 1.10 (d, 3H, J=7.0 Hz).

N-[1(R)-Carboxy-ethyl)]-α-(S)-(2-phenyl-ethyl)glycine-(L)-α-naphthylalanine, N-phenylamide (5at)

MS: m/e 524 (M$^+$) $^1$H NMR (CD$_3$OD, 200 MHz): δ8.27–7.09 (m, 17H), 5.02 (t, 1H, J 8.0 Hz), 3.83 (t, 1 H, J=7.0 Hz), 3.63 (dd, 2H, J=8.0, 4.0 Hz), 3.35 (q, 1 H, J=7.0 Hz), 2.62 (t, 2H, J=9.0 Hz), 2.09 (t, 2H, J=8.0 Hz), 1.30 (d, 3H, J=7.0 Hz).

N-[1(R)-Carboxy-ethyl)]-α-(S)-(2-phenyl-ethyl)glycine-[(L)-glutamic acid. αβ-bis-N-phenylamide] (5au)

MS: m/e 531 (M$^+$) $^1$H NMR (CD$_3$OD, 200 MHz): δ7.56 (dd, 2H, J=7.0, 1.0 Hz), 7.55 (dd, 2H, J=7.0, 1.0 Hz), 7.34–7.07 (m, 11 H), 4.62 (dd, 1 H, J=8.0, 6.0 Hz), 3.90 (t, 1 H, J=7.0 Hz), 3.62 (t, 1 H, J=7.0 Hz), 2.71 (m, 2H, J=6.0 Hz), 2.58 (t, 2H, J=7.0 Hz), 2.30 (m, 2H), 2.15 (m, 2H, J=8.0 Hz), 1.48 (d, 3H, J=7.0 Hz).

N-[1(R)-Carboxy-ethyl]-α-(S)-(2-phenyl-ethyl)glycine-(L)-leucine, N-cyclohexylamide (5av)

MS: m/e 446 (M$^+$) $^1$H NMR (CD$_3$OD, 200 MHz): δ 7.27–7.17 (m, 5H), 4.46 (dd, 1H, J=8.0, 6.0 Hz), 3.90 (t, 1 H, J=7.0 Hz), 3.54 (q, 1 H, J=7.0 Hz), 2.65 (m, 2H), 2.12 (t, 2H, J=7.0 Hz), 1.86–1.57 (m, aliphatic H's), 1.45 (d, 3H, J=7.0 Hz), 1.32–1.17 (m, aliphatic H's), 0.96 (dd, 6H, J=8.0, 6.0 Hz).

N-[(1 (R)-Carboxy-ethyl)]-α-(S)-(2-phenyl-ethyl)glycine-α-(S)-(2-(4-hydroxyphenyl)ethyl)glycine, N-phenylamide (5aw)

MS: m/e 504 (M$^+$) $^1$ H NMR (CD$_3$OD, 200 MHz): δ7.56 (dd, 2H, J=7.0, 1.0 Hz), 7.29 (dd, 2H, J=8.0, 7.0 Hz), 7.04

(d, 1 H, J=9.0 Hz), 7.29–7.05 (m, 7H), 6.70 (d, 2H, J=8.0 Hz), 4.53 (dd, 1 H, J=8.0, 6.0 Hz), 3.95 (t, 1 H, J=7.0 Hz), 3.60 (q, 1H, J=7.0 Hz), 2.70 (m, 4H), 2.17 (m, 4H), 1.50 (d, 3H, J=7.0 Hz).

N-[1(R)-Carboxy-ethyl)]-α-(S)-(2-phenyl-ethyl)glycine-(L)-phenylglycine, N-phenylamide (5ax)

MS: m/e 460 (M+) ¹H NMR (CD₃OD, 200 MHz): δ7.54 (dd, 2H, J=7.0, 1.0 Hz), 7.41–7.07 (m, 13H), 5.63 (s, 1H), 4.01 (t, 1H, J=7.0 Hz), 3.56 (q, 1H, J=7.0 Hz), 2.80 (m, 2H), 2.17 (m, 2H), 1.42 (d, 3H, J=7.0 Hz).

N-[1(R)-Carboxy-ethyl]-α-(S)-(2-phenyl-ethyl)glycine-[(L)-glutamic acid. Nδ-benzylamide, Nα-phenylamide] (5ay)

MS: m/e 545 (M+) ¹H NMR (CD₃OD, 200 MHz): δ7.56 (dd, 2H, J=7.0, 1.0 Hz), 7.33–7.09 (m, 13H), 4.58 (dd, 1H, J=8.0, 6.0 Hz), 4.37 (s, 2H), 3.91 (t, 1H, J=7.0 Hz), 3.61 (q, 1H, J=7.0 Hz), 2.72 (m, 2H), 2.44 (t, 2H, J=7.0 Hz), 2.17 (m, 2H), 1.47 (d, 3H, J=7.0 Hz).

N-[1(R)-Carboxy-ethyl)]-α-(S)-(2-phenyl-ethyl)glycine-(L)-Ornithine, N-phenylamide (5az)

MS: m/e 441 (M+) ¹H NMR (CD₃OD, 200 MHz): δ7.47 (dd, 2H, J=7.0, 1.0 Hz), 7.23–7.00 (m, 8H), 4.62 (dd, 1H, J=8.0, 5.0 Hz), 3.27 (t, 1H, J=7.0 Hz), 3.14 (q, 1H, J=7.0 Hz), 2.96 (m, 2H), 2.69 (t, 2H, J=8.0 Hz), 2.01–1.78 (m, 6H), 1.30 (d, 3H, J=7.0 Hz).

N-[1(R)-Carboxy-ethyl]-α-(S)-(2-phenyl-ethyl)glycine-(L)-arginine, N-phenylamide (5bc)

MS: m/e 483 (M+) ¹H NMR (CD₃OD, 200 MHz): δ7.56 (dd, 2H, J=7.0, 1.0 Hz), 7.29–7.05 (m, 8H), 4.55 (dd, 1H, J=8.0, 6.0 Hz), 3.39 (t, 1H, J=7.0 Hz), 3.22 (m, 3 H), 2.68 (t, 2H, J=8.0 Hz), 2.05–1.70 (m, 6H), 1.32 (d, 3H, J=7.0 Hz).

N-[1(R)-Carboxy-ethyl)]-α-(S)-(2-phenyl-ethyl)glycine-α-(S)-(3-phenylpropyl)glycine, N-phenylamide (5bb)

MS: m/e 502 (M+) ¹H NMR (CD₃OD, 200 MHz): δ7.56 (dd, 2H, J=7.0, 1.0 Hz), 7.33–7.08 (m, 13H), 4.56 (dd, 1H, J=9.0, 7.0 Hz), 3.98 (t, 1H, J=7.0 Hz), 3.59 (q, 1H, J=7.0 Hz), 2.68 (m, 4H), 2.15 (m, 2H, J=8.0 Hz), 1.80 (m, 4H), 1.46 (d, 3H, J=7.0 Hz).

N-[1(R)-carboxy-ethyl]-α-(S)-(2-phenyl-ethyl)glycine-α-(S)-n-octylglycine, N-phenylamide (5de)

MS: m/e 496 (M+) ¹H NMR (CD₃OD, 200 MHz): δ7.56 (dd, 2H, J=7.0, 1.0 Hz), 7.33–7.08 (m, 8H), 4.52 (dd, 1H, J=8.0, 6.0 Hz), 3.99 (t, 1H, J=7.0 Hz), 3.60 (q, 1H, J=7.0 Hz), 2.71 (m, 2H), 2.15 (m, 2H), 1.84 (m, 2H), 1.48 (d, 3H, J=7.0 Hz), 1.44–1.36 (m, 12H), 1.28 (t, 2H, J=7.0 Hz).

N-[1(R)-Carboxy-ethyl]-α-(S)-(2-phenyl-ethyl)glycine-(L)-leucine, N-(4-carboxyphenyl)amide (5cp)

MS: m/e 484 (M+1); 506(M+Na); 544 (M+K). 1H NMR (CD₃OD),200MHz): δ8.02–7.76 (2d,4H); 7.26 (m,5H); 4.72 (dd,1H); 4.12 (dd,1H); 3.94 (q,1H); 2.78 (m,2H); 2.22 (m,2H); 1.80 (m,3H); 1.60 (d,3H); 1.08 (2d,6H).

N-[1(R)-Carboxy-ethyl]-α-(S)-(2-phenyl-ethyl)glycine-(L)-leucine, N-(4-trifluoromethylphenyl)amide (5cv)

MS: m/e 508(M+1); 529(M+Na) ¹H NMR (CD₃OD),200 MHz): δ7.86–7.62 (2d,4H); 7.26 (m,5H); 4.72 (dd,1H); 4.04 (dd,1H); 3.66 (q,1H); 2.74 (m,2H); 2.22 (m,2H); 1.80 (m,3H); 1.56 (m,3H); 1.08 (2d,6H).

N-[1(R)-Carboxy-ethyl]-α-(S)-(2-phenyl-ethyl)glycine-(L)-leucine, N-(3-pyridyl)amide (5cy)

MS: m/e 441(M+1); 463 (M+Na) 1H NMR (CD₃OD),200 MHz): δ8.86 (d,1H); 8.30 (dd,1H); 8.18 (m,1H); 7.46 (m,1H); 7.26 (m,5H); 4.72 (dd,1H); 4.04 (dd,1H); 3.66 (q,1H); 2.78 (m,2H); 2.22 (m,2H); 1.84 (m,3H); 1.56 (d,3H); 1.08 (2d,6H).

N-[1(R)-Carboxy-ethyl]-α-(S)-(2-phenyl-ethyl)glycine-(L)-leucine, N-(benzthiazol-2-yl)amide (5db)

MS: m/e 498 (M+1) ¹H NMR (CD₃OD),200 MHz): δ7.90–7.18 (m,9H); 4.84 (dd,1H); 4.10 (dd,1H); 3.70 (q,1H); 2.78 (m,2H); 2.24 (m,2H); 1.84 (m,3H); 1.56 (d,3H); 1.08 (2d,6H).

EXAMPLE 4

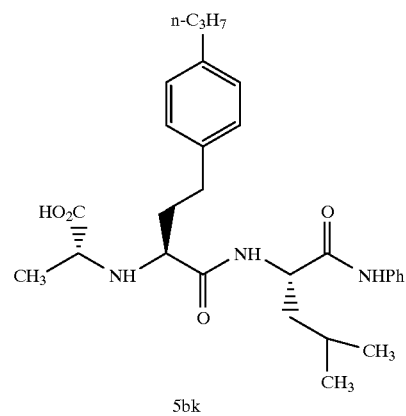

5bk

Employing the procedure outlined in Method D, N-benzyloxycarbo-ethyl dipeptide 10 was prepared and converted to compound 5bk using methodology described in Example 1 for the preparation of 5a.

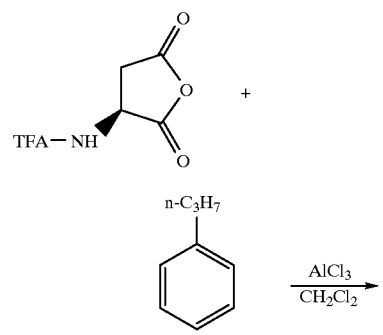

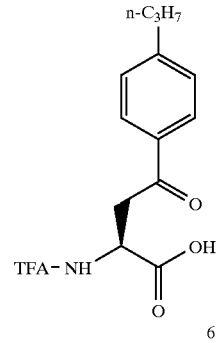

6

N-Trifluoroacetyl-α-(S)-(2-(4-n-propylphenyl)-2-oxoethyl) glycine (6)

Aluminum chloride (1.7 gm, 7.5 mmol) was added to an ice cooled solution of N-trifluoroacetyl-(L)-aspartic acid anhydride (1.0 gm, 4.7 mmol) and n-propylbenzene (1.4 mL, 10 mmol) in dry methylene chloride (15 mL) under a dry nitrogen atmosphere. The solution was stirred at room temperature for 5 days and then quenched in a mixture of ice/ 2N HCl/ethyl acetate. The mixture was extracted with ethyl acetate (3×50 mL), dried over anhydrous sodium sulfate, and evaporated in vacuo. The residue was partitioned between acetonitrile (100 mL) and hexanes (500 mL).

The acetonitrile layer was separated, washed with hexanes (2×500 mL), and dried over anhydrous sodium sulfate. The solvent was evaporated in vacuo and the residue dissolved in ethyl acetate (150 mL). Activated charcoal (10 gm) was added, the solution filtered through celite filter aid, and evaporated in vacuo. The product was crystallized from ethyl acetate/hexanes (0.67 gm, 43% yield). $^1$H NMR (CDCl$_3$, 200 MHz): δ7.84 (d, 2H, J=8.0 Hz), 7.28 (d, 2H, J=8.0 Hz), 5.0 (m, 1H, J=4.0 Hz), 3.92 (ABq/d, 2H, J=18 Hz, J=5 Hz), 2.65 (t, 2H, J=6.0 Hz), 1.65 (m, 2H, J=8.0 Hz), 0.94 (t, 3H, J=6.0 Hz)

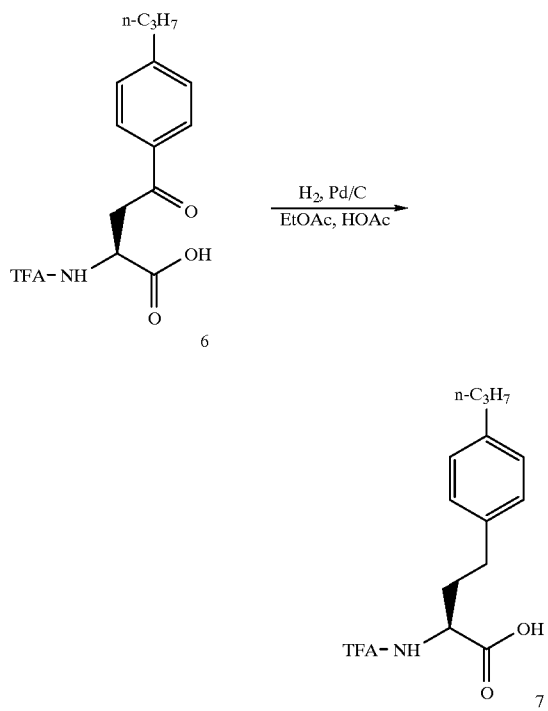

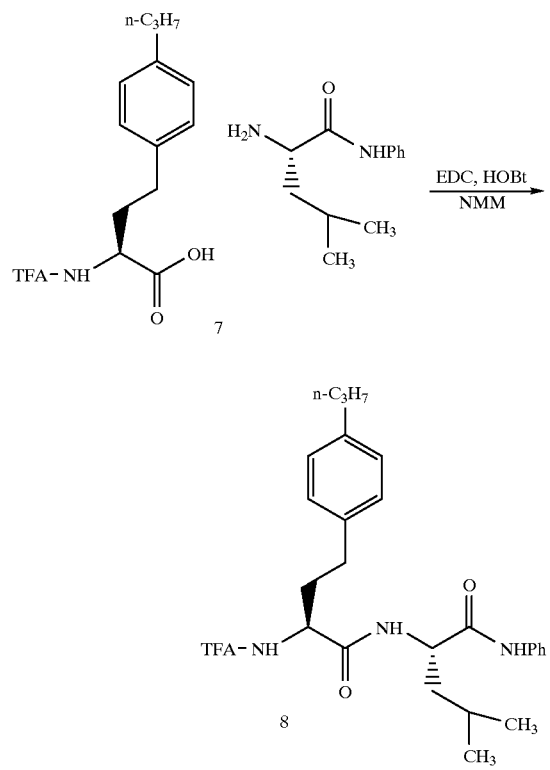

N-Trifluoroacetyl-α-(S)-(2-(4-n-propylphenyl)ethyl)glycine (7)

A solution of N-trifluoroacetyl-α-(S)-(2-(4-n-propylphenyl)-2-oxoethyl)glycine 6 (140 mg, 0.43 mmol) in ethyl acetate (10 mL) containing acetic acid (0.25 mL) and 10% palladium on carbon (10 mg) was stirred under one atmosphere of hydrogen gas. After two days, the catalyst was filtered off and fresh catalyst was added and the reaction stirred under hydrogen overnight. The mixture was filtered and the solvent evaporated in vacuo to yield the product 7 (127 mg, 93% yield).

MS: m/e 318 (M+1), 340 (M+Na) $^1$H NMR (CD$_3$OD, 200 MHz): δ7.08 (s, 4H), 4.37 (dd, 1H, J=4.0 Hz), 2.65 (m, 2H), 2.54 (t, 2H, J=7.0 Hz), 2.3–2.0 (br. m, 2H), 1.62 (m, 2H, J=8.0 Hz), 1.92 (t, 3H, J=8.0 Hz)

N-(Trifluoroacetyl)-α-(S)-(2-(4-n-propylphenyl)ethyl) glycine-(L)-Leucine, N-phenylamide (8)

A solution of N-trifluoroacetyl-α-(S)-(2-(4-n-propylphenyl)ethyl)glycine 7 (127 mg, 0.40 mmol) in methylene chloride (10 mL) was cooled to 0° C. under a dry nitrogen atmosphere. N-methyl morpholine (48 μL, 0.44 mmol) was added followed by N-hydroxybenztriazole (81 mg, 0.6 mmol). After stirring for 15 minutes, (L)-Leucine, N-phenylamide (108 mg, 0.5 mmol) was added followed by N-ethyl-N'-(3-diethylaminopropyl)-carbodiimide (EDAC, 115 mg, 0.6 mmol). The solution was stirred overnight at room temperature, diluted with ethyl acetate (100 mL) and washed with 2N HCl (3×20 mL), saturated sodium bicarbonate solution (2×20 mL), and water (20 mL). The solution was dried over anhydrous sodium sulfate and evaporated in vacuo. The product was purifed by preparative thin layer chromatography on silica gel plates eluted twice with 1.5% methanol in chloroform, then rechromatographed with 1% methanol in chloroform (122 mg, 61% yield).

$^1$H NMR (CD$_3$OD, 400 MHz): δ7.53 (d, 2H, J=7.7 Hz), 7.28 (m, 2H), 7.06 (m, 5H), 4.54 (m, 1H), 4.42 (m, 1H), 2.7–2.6 (m, 2H), 2.52 (t, 2H, J=6.0 Hz), 2.2–2.0 (br. m, 2H), 1.8–1.6 (br. m, 2H), 1.59 (m, 2H, J=8.0 Hz), 0.97 (dd, 6H, J=6.0 Hz), 0.91 (t, 3H, J=6.4 Hz)

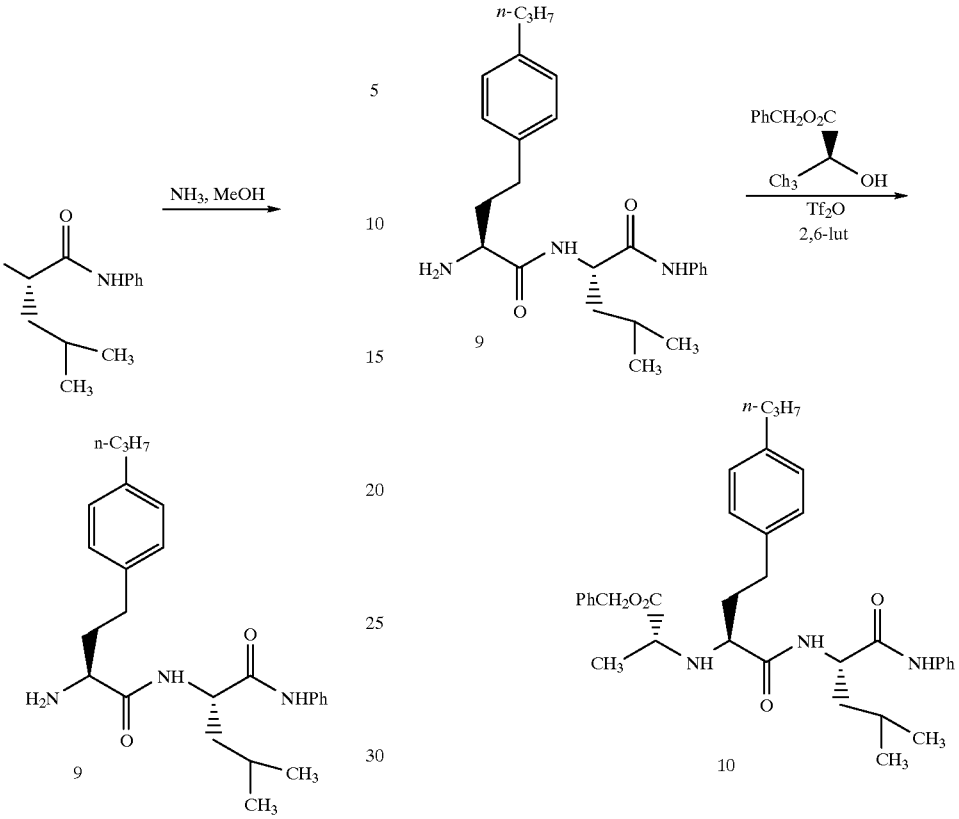

α-(S)-(2-(4-n-Propylphenyl)ethyl)glycine-(L)-leucine, N-phenylamide (9)

Ammonia gas was bubbled into methanol (20 mL) at −20° C. for 30 minutes then placed in a pressure tube with N-trifluoroacetyl-α-(S)-(2-(4-n-propylphenyl)ethyl) glycine-(L)-leucine, N-phenylamide 8 (120 mg, 0.23 mmol), sealed, and stirred at room temperature for 5 days. The tube was cooled to −20° C. before opening and then the solvent was evaporated in vacuo. The product was purified by preparative thin layer chromatography on silica gel eluted with 2% methanol in chloroform (95 mg, 100% yield).

$^1$H NMR (CD$_3$OD, 400 MHz): δ7.55 (d, 2H, J=8.6 Hz), 7.29 (t, 2H, J=8.5 Hz), 7.1–7.0 (m, 5H), 4.56 (m, 1H), 3.4 (t, 1H J=6.0 Hz), 2.61 (t, 2H, J=8.0 Hz), 2.51 (t, 2H, J=7.0 Hz), 2.0–1.6 (br. m, 4H), 1.59 (m, 2H, J=7.5 Hz), 0.99 (t, 6H, J=6.0 Hz), 0.90 (t, 3H, J=7.4 Hz)

N-[1(R)-Benzyloxycarbonyl-ethyl]-α-(S)-(2-(4-n-propylphenyl)ethyl)glycine-(L)-leucine, N-phenylamide (10)

To a solution of benzyl (L)-lactate (39 mg, 0.21 mmol) in methylene chloride (2 mL) at 0° C. under a dry nitrogen atmosphere was added 2,6-lutidine (28 μL, 0.24 mmol) followed by triflic anhydride (39 μL, 0.23 mmol). After stirring for 10 minutes at 0° C., a solution of diisopropylethylamine (41 μL, 0.24 mmol) and α-(S)-(2-(4-n-propylphenyl)ethyl)glycine-(L)-Leucine, N-Phenylamide 9 (95 mg, 0.24 mmol) in methylene chloride (1 mL) was added. The solution was stirred at room temperature overnight, diluted with methylene chloride (20 mL), and washed successively with water (2×5 mL), saturated sodium bicarbonate (2×5 mL), and saturated salt solution (5 mL). The solution was dried over anhydrous sodium sulfate and evaporated in vacuo. The product was purified by HPLC on silica gel eluted with 2% acetone in methylene chloride (103 mg, 85% yield).

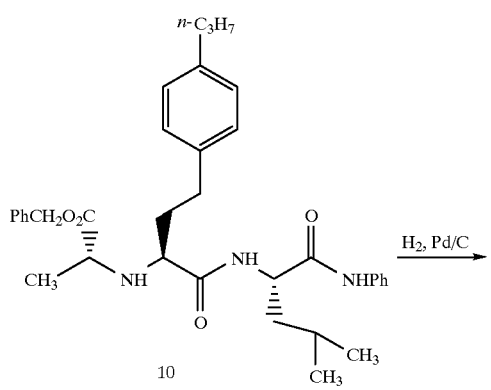

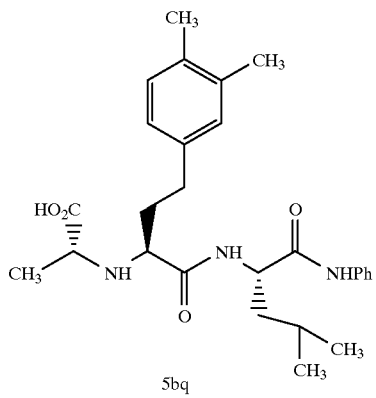

EXAMPLE 5

Employing the procedure outlined in Method E, dipeptide 14 was prepared and converted to compound 5bq using methodology described in Example 4 for the preparation of 5bk.

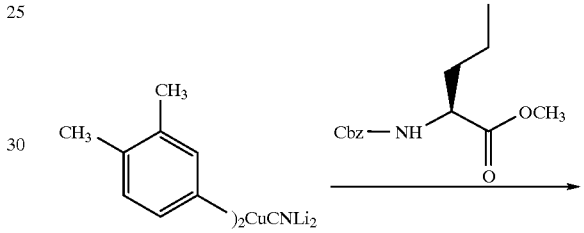

N-[1(R)-Carboxyethyl]-α-(S)-(2-(4-n-propylphenyl)ethyl) glycine-(L)-leucine, N-phenylamide (5bk)

A solution of N-[1(R)-benzyloxycarbonylethyl]-a-(S)-(2-(4-n-propylphenyl)ethyl)glycine-(L)-leucine, N-phenylamide 10 (103 mg, 0.18 mmol) in ethyl acetate (10 mL) containing Peariman's catalyst (15 mg) was stirred under 1 atmosphere of hydrogen gas overnight. The mixture was filtered and the solvent evaporated in vacuo to give 5bk (70 mg, 82% yield):

MS: m/e 483 (M$^+$1) $^1$H NMR (CD$_3$OD, 200 MHz): δ7.56 (d, 2H, J=7.7 Hz), 7.37–7.28 (m, 3H), 7.09–7.05 (m, 4H), 5.15 (dd, 1H, J=7.0, 2.0 Hz), 4.67 (t, 1H, J=6.0 Hz), 4.00 (t, 1H, J=6.0 Hz), 3.75 (m, 1 H), 2.68 (br. m, 2H), 2.51 (t, 2H, J=7.0 Hz), 2.12 (m, 2H), 1.80–1.58 (m, 6H), 1.51 (d, 3H, J=7.0 Hz), 1.31 (br. m, 4H), 1.01 (dd, 6H, J=6.0 Hz), 0.90 (t, 3H, J=7.0 Hz).

The following additional compounds were prepared according to the method of Example 4.

[N-(1 (R)-Carboxy-ethyl)-α-(S)-[2-(4-propylphenyl)ethyl]] glycine-(L)-arginine, N-phenylamide (5by)

MS: m/e 525 (M+1) $^1$H NMR (CD$_3$OD, 400 MHz): δ7.57 (d, 2H, J=8 Hz), 7.25 (t, 2H, J=8 Hz), 7.11–7.01 (m, 5H), 4.52 (dd, 1H, J=8.5, 4.5 Hz), 3.27–3.18 (m, 3H), 3.15 (q, 1H, J=7 Hz), 2.63 (t, 2H, J=7.5 Hz), 2.51 (t, 2H, J=7 Hz), 2.02–1.80 (m, 4H), 1.78–1.66 (m, 2H), 1.59 (hextet, 2H, J=7 Hz), 1.27 (d, 3 H, J=7 Hz), 0.90 (t, 3H, J=7 Hz).

N-Benzyloxycarbonyl-α-(S)-(2-(3,4-dimethylphenyl)ethyl) glycine, methyl ester (11)

A solution of n-butyl lithium in hexanes (1.6N, 2.5 mL) was added to 3,4-dimethyliodobenzene (870 mg, 4 mmol) in a 25 mL round bottom flask that had been cooled to −78° C. under a dry nitrogen atmosphere. The solution was slowly warmed to 40° C. and stirred for 1 hour. The solution was cooled to 0° C. and slowly transferred via cannula to a dry flask under dry nitrogen atmosphere containing copper(I) cyanide (179 mg, 2 mmol) in 5 mL THF. The mixture was stirred until homogeneous and the solvent evaporated with a stream of nitrogen gas. The residue was redissolved in THF and stirred for 1 hour at 0° C. to yield a greenish solution.

Approximately half of the THF cuprate solution (~1.4 mmol) was diluted in dry THF (20 mL) and cooled to 0° C. This solution was slowly added via a syringe pump over a period of 1 hour to a solution of N-carbobenzyloxy-α-(S)-(2-iodoethyl)lglycine, methyl ester (277 mg, 0.70 mmol) in THF (5 mL). The solution was stirred at room temperature for 5 hours. The reaction was quenched with 10% ammonium chloride solution (5 mL) and extracted with methylene chloride (3×20 mL). The solution was dried over anhydrous magnesium sulfate and the solvent and excess iodoxylene evaporated under high vacuum. The product was purified by flash column chromatography on silica gel eluted with 20% ethyl acetate in hexanes (78 mg, 31% yield).

$^1$H NMR (CDCl$_3$, 200 MHz): δ7.36 (bs, 5H), 7.05 (d, 1H, J=7.0 Hz), 6.08–6.94 (m, 2H,), 5.36 (d, 1H, J=8Hz), 5.13 (s, 2H,), 4.05 (bm, 1H, ), 3.73 (s, 3H,), 2.6 (t, 2H, J=9.0 Hz),.2.23 (s, 6H), 2.15 (m, 1H, J=8 Hz), 1.95 (m, 1H, J=8 Hz),

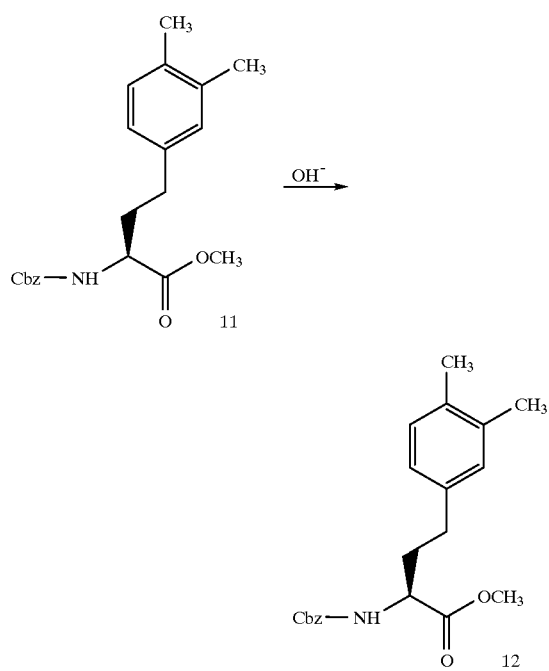

N-Benzyloxycarbonyl-α-(S)-(2-(3,4-dimethylphenyl)ethyl) glycine (12)

A solution of N-carbobenzyloxy-α-(S)-(3,4-dimethylphenethyl)glycine, methyl ester 11 (209 mg, 0.59 mmol), was disolved in 6 mL of methanol and 3 mL of water. The solution was degased and flushed with nitrogen. One equivalent (24 mg) of LiOH was added to the solution, the flask sealed and stirred overnight at room temperature. The solution was acidified with 1.1 equivalents of acetic acid (39 mg) and the solvent evaporated in vacuo. The residue was washed with water and filtered. The precipitate was dried in vacuo (204 mg, 100% yield). The product was used without further purification.

$^1$H NMR (CD$_3$OD, 200 MHz): δ7.36 (br m, 5H), 7.0–6.8 (m, 3H, J=7.0 Hz), 5.08 (s, 2H), 5.13 (s, 2H), 4.08 (br m, 1H), 2.56 (t, 2H, J=9.0 Hz),.2.19 (s, 6H), 2.15–1.9 (bm, 2H)

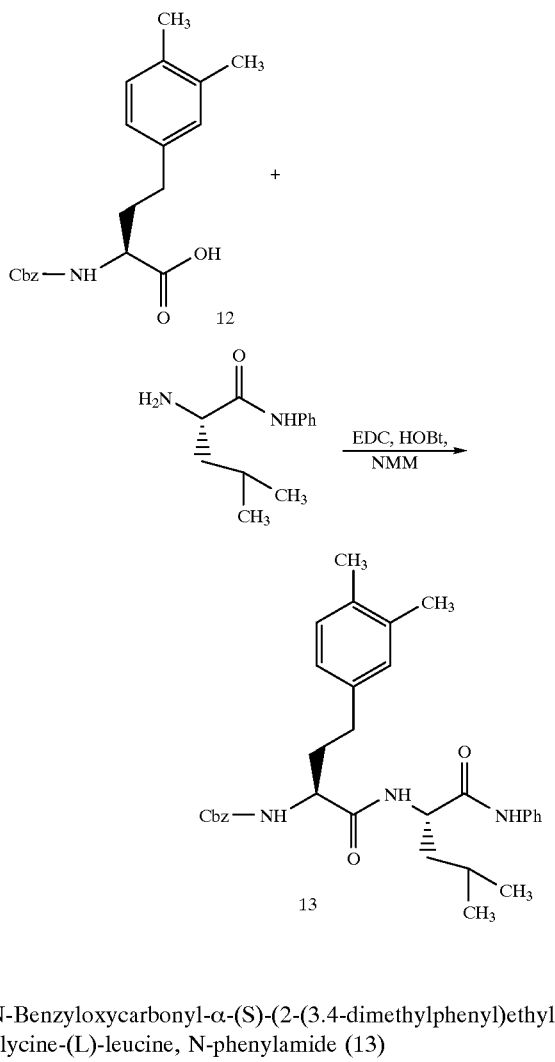

N-Benzyloxycarbonyl-α-(S)-(2-(3.4-dimethylphenyl)ethyl) glycine-(L)-leucine, N-phenylamide (13)

A solution of N-Carbobenzyloxy-α-(S)-(3,4-dimethylphenethyl)glycine 12 (207 mg, 0.55 mmol), (L)-leucine, N-phenylamide (125 mg, 0.61 mmol), N-hydroxybenztriazole (87 mg, 0.66 mmol), and N-methyl morpholine (130 μL, 1.1 mmol) in THF (3 mL) was stirred at room temperature for 10 minutes. EDAC (158 mg, 0.83 mmol) was added and the solution stirred for 4 hours. Methylene chloride (25 mL) was added and the solution washed successively with 2N HCl (3×5 mL) and saturated sodium bicarbonate solution (3×5 mL). After drying over anhydrous magnesium sulfate, the solvent was evaporated in vacuo and the product purified by flash column chromatography on silica gel eluted with 2% ethyl acetate in methylene chloride (148 mg, 53% yield).

$^1$H NMR (CD$_3$OD, 200 MHz): δ7.56 (d, 2H, J=7.7 Hz), 7.42–7.28 (m, 7H), 7.16–6.83 (m, 4H), 5.15 (S, 2H), 4.60 (t, 1H, J=6.0 Hz), 4.16 (t, 1H, J=6.0 Hz), 2.6 (br. m, 2H), 2.2 (S, 6H), 2.2–1.8 (m, 2H), 1.8–1.6 (br m, 2H),1.31 (br m, 1H), 1.01 (s, 6H, J=6.0 Hz).

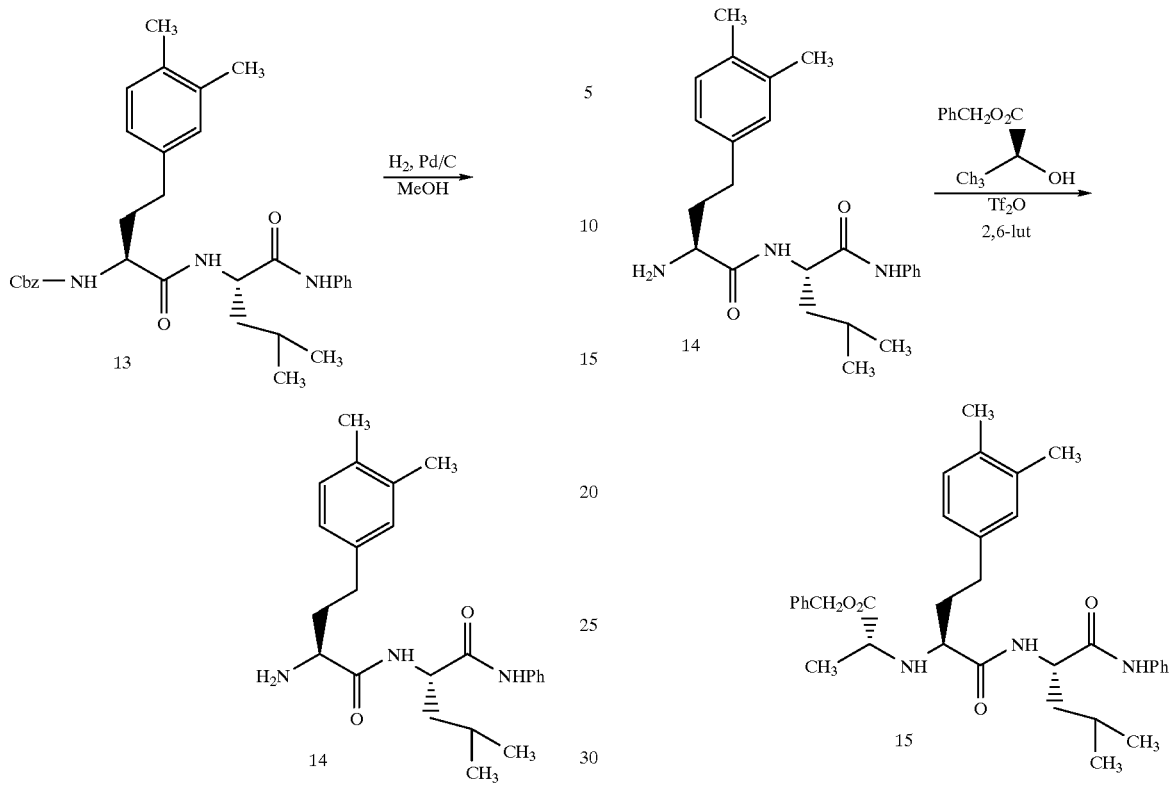

α-(S)-(2-(3,4-dimethylphenyl)ethyl)glycine-(L)-leucine, N-phenylamide (14)

To a solution of 3 ml of methanol and N-carbobenzyloxy-α-(S)-(3,4-dimethylphenethyl)glycine-(L)-leucine, N-phenylamide (148 mg) was added 10 mg of 10% palladium on carbon in a 10 ml round bottom flask fifted with a stirring bar and rubber septum. The flask was flushed with hydrogen via syringe attached to a balloon reservoir. Stirring was continued for 1 hr, during which the starting material was converted to product and the reaction mixture became homogeneous. Filtration through a 2 micron filter removed the palladium catalyst and the methanol solvent was removed under reduced pressure. The product was recovered (89 mg, 98% yield) and used in the subsequent step without purification.

$^1$H NMR (CD$_3$OD, 200 MHz): δ7.56 (d, 2H, J=7.7 Hz), 7.42–7.28 (m, 2H), 7.18–7.1 (m, H), 6.8 (S, 3H), 4.63 (t, 1H, J=6.0 Hz), 3.42 (t, 1H, J=6.0 Hz), 2.6 (t, 2H, J=6 Hz, ), 2.2 (S, 6H), 2.1–1.8 (m, 2H), 1.8–1.6 (br m, 2H), 1.31 (br m, 1H), 1.01 (m, 6H, ).

N-[1(R)-Benzyloxycarbonyl-ethyl]-α-(S)-(2-(3,4-dimethylphenyl)ethyl)glycine-(L)-leucine, N-phenylamide (15)

To a solution of benzyl (L)-lactate (52 mg, 0.28 mmol) in methylene chloride (5 mL) at 0° C. under a dry nitrogen atmosphere was added 2,6-lutidine (35 μL, 0.30 mmol), stirred for 5 minutes and then followed by triflic anhydride (48 μL, 0.28 mmol). After stirring for 10 minutes at 0° C., a solution of diisopropylethylamine (51 μL, 0.29 mmol) and α-(S)-(3,4-dimethylphenethyl)glycine-(L)-leucine, N-phenylamide 14 (104 mg, 0.26 mmol) in methylene chloride (5 mL) was added. The solution was stirred at room temperature overnight, diluted with methylene chloride (20 mL), and washed successively with water (2×5 mL), saturated sodium bicarbonate (2×5 mL). The solution was dried over anhydrous sodium sulfate and evaporated in vacuo. The product was purified by HPLC on silica gel eluted with 3% ethyl acetate in methylene chloride (47 mg, 32% yield).

$^1$H NMR (CD$_3$OD, 200 MHz): δ7.56 (d, 2H, J=7.7 Hz), 7.37–7.28 (m, 7H), 7.15–7.1 (d, 4H, J=7.0), 7.0–6.85 (m,3H), 5.13 (s, 2H), 4.6 (bs, 1H), 3.45 (t, 1H, J=6.0 Hz), 2.6 (t., 2H, J=6 Hz), 2.2 (s, 6H), 1.95–1.6 (m, 6H), 1.3 (d, 3H, J=7 Hz), 0.98 (m, 6H).

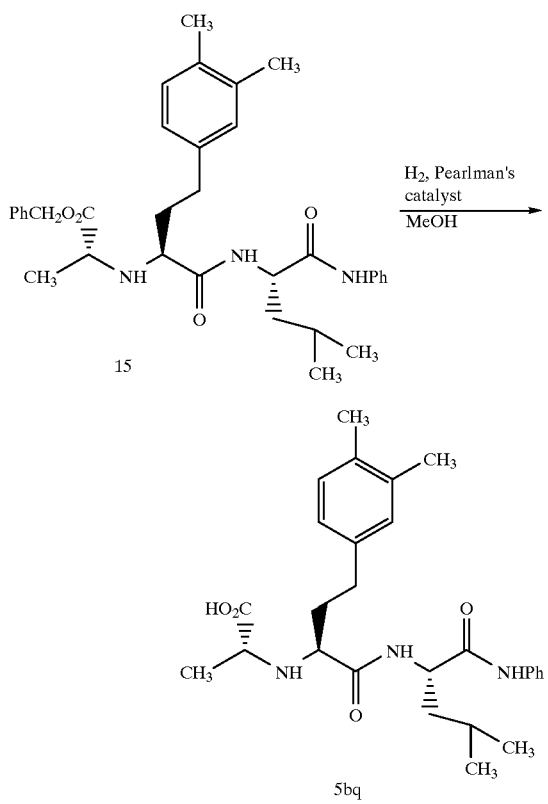

N-[1 (R)-Carboxy-ethyl]-α-(S)-(2-(3,4-dimethylphenyl)ethyl)glycine-(L)-leucine, N-phenylamide (5bq)

To a solution of 47 mg of aminoester in 1 mL of methanol was added 2 mg of Pearlman's catalyst. After 3 hours of vigorous stirring under an atmosphere of hydrogen, the mixture was filtered through 2 micron nylon filter pack and concentrated in vacuo to give 41 g of 5bq as a colorless solid:

$^1$H NMR (CD$_3$OD, 200 MHz): δ7.56 (d, 2H, J=7.7 Hz), 7.37–7.28 (m, 2H), 7.15–7.1 (d, 1H, J=7.0), 7.0–6.85 (m,3H), 4.7 (bs, 1H), 4.0 (bm, 1H), 3.60 (t, 1H, J=6.0 Hz), 2.6 (t., 2H, J=6 Hz), 2.2 (s, 6H), 2.2–2.0 (m, 4H), 1.75 (m, 5H), 1.3 (d, 3H, J=7 Hz), 0.98 (m, 6H).

What is claimed is:
1. A compound of Formula Ia

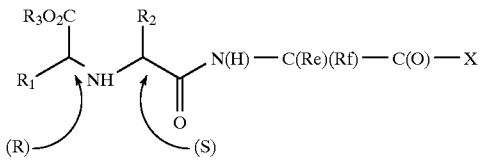

or a pharmaceutically acceptable salt thereof wherein:
R$_1$ is substituted C$_{1-6}$alkyl, wherein the substituent is selected from the group consisting of:
(a) hydrogen,
(b) carboxy,
(c)

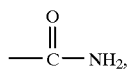

(d) aryl wherein the aryl group is selected from the group consisting of:
(1) phenyl,
(2) naphthyl,
(3) pyridyl,
(4) furyl,
(5) pyrryl,
(6) thienyl,
(7) isothiazolyl,
(8) imidazolyl,
(9) benzimidazolyl,
(10) tetrazolyl,
(11) pyrazinyl,
(12) pyrimidyl,
(13) quinolyl,
(14) isoquinolyl,
(15) benzofuryl,
(16) isobenzofuryl,
(17) benzothienyl,
(18) pyrazolyl,
(19) indolyl,
(20) isoindolyl,
(21) purinyl,
(22) carbazolyl,
(23) isoxazolyl,
(24) thiazolyl,
(25) oxazolyl,
(26) benzthiazolyl,
(27) benzoxazolyl,
and mono and di-substituted aryl as defined above in items (1) to (27) wherein the substitutents are independently selected from, C$_{1-6}$alkyl, C$_{1-6}$alkyloxy, halo, hydroxy, amino, C$_{1-6}$alkylamino, amino C$_{1-6}$alkyl, carboxyl, carboxyl C$_{1-6}$alkyl, and C$_{1-6}$alkylcarbonyl,
(e)

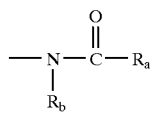

wherein R$_a$ and R$_b$ are each independently hydrogen; aryl and mono and di-substituted aryl as defined above (d);

or substituted C$_{1-6}$alkyl wherein the substitutent is selected from hydroxy, halo, and phenyl, or wherein R$_a$ and R$_b$ are joined such that together with the nitrogen and carbon atoms to which they are attached, there is formed a lactam or benzolactam ring wherein the lactam portion thereof is a ring of up to 8 atoms, said lactam or benzolactam have a single hetero atom,
(f)

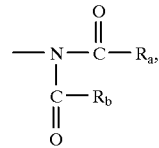

wherein R$_a$ and R$_b$ are each independently hydrogen; aryl and mono and di-substituted aryl as defined above (d); or substituted C$_{1-6}$alkyl wherein the substituent is selected from hydroxy, halo, and phenyl, or wherein R$_a$ and R$_b$ are joined such that together with the nitrogen and carbon atoms to which they are attached, there is formed a lactam or benzolactam ring wherein the lactam portion thereof is a ring of up to 8 atoms, said lactam or benzolactam have a single hetero atom, and
(g) amino and substituted amino wherein the substituent is selected from C$_{1-6}$ alkyl and C$_{6-10}$ aryl where aryl is defined in (d);
R$_2$ is CHR$_c$R$_d$ wherein
R$_c$ is selected from the group consisting of:
(a) H,
(b) C$_{1-3}$alkyl and
(c) hydroxyl, and
R$_d$ is aryl C$_{1-2}$ alkyl or aryl substituted C$_{1-2}$ alkyl wherein the substituent is C$_{1-3}$alkyl or hydroxy, and wherein the aryl group is phenyl, wherein the substituents are independently selected from C$_{1-6}$alkyl, C$_{1-6}$alkyloxy, halo, hydroxy, amino, C$_{1-6}$alkylamino, amino C$_{1-6}$alkyl, carboxyl, carboxyl C$_{1-6}$alkyl and C$_{1-6}$alkylcarbonyl;
R$_3$ is selected from the group consisting of:
(a) H,
(b) C$_{1-10}$alkyl and
(c) aryl or aryl C$_{1-3}$alkyl, wherein the aryl group is selected from the group consisting of:
(1) phenyl and
(2) substituted phenyl, wherein the substituent is selected from carboxy, carboxy C$_{1-3}$alkyl, aminocarbonyl and C$_{1-6}$alkylaminocarbonyl;
R$_e$ and R$_f$ are individually selected from:
(a) hydrogen,
(b) C$_{1-6}$alkyl,
(c) mercapto C$_{1-6}$alkyl,
(d) hydroxy C$_{1-6}$alkyl,
(e) carboxy C$_{1-6}$alkyl,
(f) amino substituted C$_{1-6}$alkyl,
(g) aminocarbonyl C$_{1-6}$alkyl,
(h) mono- or di-C$_{1-6}$alkyl amino C$_{1-6}$alkyl,
(i) guanidino C$_{1-6}$alkyl,
(j) substituted phenyl C$_{1-6}$alkyl, wherein the substituent is hydrogen, hydroxy, carboxy, C$_{1-4}$alkyl, or C$_{1-4}$alkyloxy,
(k) substituted indolyl C$_{1-6}$alkyl, wherein the substituent is hydrogen, hydroxy, carboxy, C$_{1-4}$alkyl, or C$_{1-4}$alkyloxy,
(l) substituted imidazolyl C$_{2-6}$alkyl wherein the substituent is hydrogen, hydroxy, carboxy, C$_{1-4}$alkyl, or C$_{1-4}$alkyloxy, (m) substituted pyridyl $C_{1-6}$allyl wherein the substituent is hydrogen, hydroxy, carboxy, $C_{1-4}$alkyl, or $C_{1-4}$alkyloxy and (n) substituted pyridylamino $C_{1-6}$alkyl wherein the substituent is hydrogen, hydroxy, carboxy, $C_{1-4}$alkyl, or $C_{1-4}$alkyloxy;

X is

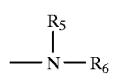

wherein $R_5$ is selected from the group consisting of:
(a) H,
(b) $C_{1-10}$alkyl and
(c) aryl or aryl $C_{1-6}$alkyl, wherein the aryl group is selected from the group consisting of:
(1) phenyl,
(2) naphthyl,
(3) pyridyl,
(4) pyrryl,
(5) furyl,
(6) thienyl,
(7) isothiazolyl,
(8) imidazolyl,
(9) benzimidazolyl,
(10) tetrazolyl,
(11) pyrazinyl,
(12) pyrimidyl,
(13) quinolyl,
(14) isoquinolyl,
(15) benzofuryl,
(16) isobenzofuryl,
(17) benzothienyl,
(18) pyrazolyl,
(19) indolyl,
(20) isoindolyl,
(21) purinyl,
(22) carbazolyl,
(23) isoxazolyl,
(24) benzthiazolyl,
(25) benzoxazolyl,
(26) thiazolyl and
(27) oxazolyl and $R_6$ is
aryl, wherein the aryl group is selected from the group consisting of:
(1) phenyl,
(2) naphthyl,
(3) pyridyl,
(4) pyrryl,
(5) furyl,
(6) thienyl,
(7) isothiazolyl,
(8) imidazolyl,
(9) benzimidazolyl,
(10) tetrazolyl,
(11) pyrazinyl,
(12) pyrimidyl,
(13) quinolyl,
(14) isoquinolyl,
(15) benzofuryl,
(16) isobenzofuryl,
(17) benzothienyl,
(18) pyrazolyl,
(19) indolyl,
(20) isoindolyl,
(21) purinyl,
(22) carbazolyl,
(23) isoxazolyl,
(24) benzthiazolyl,
(25) benzoxazolyl,
(26) thiazolyl and
(27) oxazolyl.

2. A compound according to claim 1 wherein $R_1$ is substituted $C_{1-6}$alkyl, wherein the substituent is selected from the group consisting of:
(a) hydrogen,
(b) carboxy,
(c)

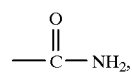

(d) aryl wherein the aryl group is selected from the group consisting of:
(1) phenyl,
(2) naphthyl,
(3) thienyl,
(4) imidazolyl,
(5) benzimidazolyl,
(6) pyrimidyl,
(7) benzofuryl,
(8) benzothienyl and
(9) indolyl,
and mono and di-substituted aryl as defined above in items (1) to (9) wherein the substituents are independently $C_{1-6}$alkyl, $C_{1-6}$alkyloxy, halo, hydroxy and $C_{1-6}$alkylcarbonyl, and
(e)

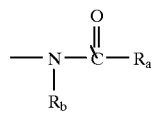

wherein $R_a$ and $R_b$ are each independently hydrogen, aryl wherein the aryl group is selected from the group consisting of:
(1) phenyl,
(2) naphthyl,
(3) thienyl,
(4) imidazolyl,
(5) benzimidazolyl,
(6) pyrimidyl,
(7) benzofuryl,
(8) benzothienyl and
(9) indolyl,
and mono and di-substituted aryl as defined above; or substituted $C_{1-6}$alkyl wherein the substitutent is selected from hydroxy, halo, and phenyl; or wherein $R_a$ and $R_b$ are joined such that together with the nitrogen and carbon atoms to which they are attached, there is formed a lactam or benzolactam ring wherein the lactam portion thereof is a ring up to 8 atoms, said lactam or benzolactam have a single hereto atom.

3. A compound according to claim 1 wherein:
$R_3$ is
(a) H, (b) C$_{1-10}$alkyl,
(c) phenyl, substituted phenyl, wherein the substituent is carboxy, carboxy C$_{1-3}$alkyl, amino carbonyl.

4. A compound according to claim 3 wherein

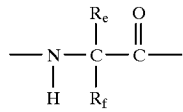

[AA] is an amino acid selected from glycine, alanine, valine, leucine, isoleucine, serine, threonine, aspartic acid, asparagine, glutamic acid, glutamine, lysine, hydroxylysine, homohistidine, arginine, phenylalanine, tyrosine, tryptophan, cysteine, methionine, ornithine, homoserine, and citrulline.

5. A compound according to claim 3 wherein
R$_e$ and R$_f$ are independently selected from
(a) hydrogen;
(b) C$_{1-4}$alkyl;
(c) mercapto C$_{1-3}$alkyl;
(d) hydroxy C$_{1-4}$alkyl;
(e) carboxy C$_{1-4}$alkyl;
(f) amino C$_{1-4}$alkyl;
(g) aminocarbonyl C$_{1-4}$alkyl;
(h) mono- or di-C$_{1-6}$alkyl amino C$_{1-4}$alkyl;
(i) guanidino C$_{1-4}$alkyl;
(j) substituted phenyl C$_{1-4}$alkyl, wherein the substituent is hydrogen, hydroxy, carboxy, or C$_{1-3}$alkyl;
(k) substituted indolyl C$_{1-4}$alkyl, wherein the substituent is hydrogen, hydroxy; carboxy, or C$_{1-3}$alkyl;
(l) substituted imidazolyl C$_{2-6}$alkyl wherein the substituent is hydrogen, hydroxy, carboxy; or C$_{1-4}$alkyl
(m) substituted pyridyl C$_{1-6}$alkyl wherein the substituent is hydrogen, hydroxy; carboxy, C$_{1-4}$alkyl, or C$_{1-4}$alkyloxy, and
(n) substituted pyridylamino C$_{1-6}$alkyl wherein the substitutent is hydrogen, hydroxy, carboxy; C$_{1-4}$alkyl, or C$_{1-4}$alkyloxy.

6. A compound according to claim 5 wherein
X is

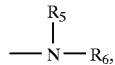

wherein R$_5$ is selected from the group consisting of:
(a) H,
(b) C$_{1-10}$alkyl and
(c) aryl or aryl C$_{1-6}$alkyl wherein the aryl group is selected from the group consisting of:
(1) phenyl,
(2) naphthyl,
(3) thienyl,
(4) imidazolyl,
(5) benzimidazolyl,
(6) pyrimidyl,
(7) benzofuryl,
(8) benzothienyl,
(9) indolyl and
(10) pyridyl; and
R$_6$ is
aryl wherein the aryl group is selected from the group consisting of:
(1) phenyl,
(2) naphthyl,
(3) thienyl,
(4) imidazolyl,
(5) benzimidazolyl,
(6) pyrimidyl,
(7) benzofuryl,
(8) benzothienyl,
(9) indolyl and
(10) pyridyl.

7. A compound according to claim 6 wherein:
R$_d$ is C$_{1-4}$alkyl aryl C$_{1-2}$alkyl; and
R$_3$ is (a) H or
(b) C$_{1-10}$alkyl.

8. A compound according to claim 6 wherein,
R$_1$ is [C$_{6-10}$]aryl C$_{1-6}$alkyl; and
R$_b$ is H.

9. A compound of formula I according to claim 8 which is:
(a) N-[1(R)-Carboxy-ethyl]-α-(S)-(2-phenyl-ethyl)glycine-(L)-leucine, N-phenylamide;
(b) N-[1(R)-Carboxy-ethyl]-α-(S)-(2-phenyl-ethyl)glycine-(L)-isoleucine, N-phenylamide;
(c) N-[1(R)-Carboxy-ethyl]-α-(S)-(2-phenyl-ethyl)glycine-(L)-alanine, N-phenylamide;
(d) N-[1(R)-Carboxy-ethyl]-α-(S)-(2-phenyl-ethyl)glycine-(L)-phenylalanine, N-phenylamide;
(e) N-[1(R)-Carboxy-ethyl]-α-(S)-(2-phenyl-ethyl)glycine-(L)-serine-O-benzyl ether, N-phenylamide;
(f) N-[1(R)-Carboxy-ethyl]-α-(S)-(2-phenyl-ethyl)glycine-(L)-tryptophan, N-phenylamide;
(g) N-[1(R)-Carboxy-ethyl]-α-(S)-(2-phenyl-ethyl)]glycine-α-(S)-(2-phenyl-ethyl)glycine, N-phenylamide;
(h) N-[1(R)-Carboxy-ethyl]-α-(S)-(2-phenyl-ethyl)glycine-(L)-norleucine, N-phenylamide;
(i) N-[1(R)-Carboxy-ethyl]-α-(S)-(2-phenyl-ethyl)glycine-(L)-valine, N-phenylamide;
(j) N-[1(R)-Carboxy-ethyl]-α-(S)-(2-phenyl-ethyl)glycine-(L)-serine, N-phenylamide Hydrochloride;
(k) N-[1(R)-Carboxy-ethyl]-α-(S)-(2-phenyl-ethyl)glycine-(L)-asparagine, N-phenylamide;
(l) N-[1(R)-Carboxy-ethyl]-α-(S)-(2-phenyl-ethyl)glycine-(L)-threonine, N-phenylamide hydrochloride;
(m) N-[1(R)-Carboxy-ethyl]-α-(S)-(2-phenyl-ethyl)glycine-(L)-lysine, N-phenylamide;
(n) N-[1(R)-Carboxy-ethyl)]-α-(S)-(2-phenyl-ethyl)glycine-(L)-glutamic acid, N-phenylamide;
(o) N-[1(R)-Carboxy-ethyl)]-α-(S)-(2-phenyl-ethyl)glycine-(L)-tyrosine, N-phenylamide hydrochloride;
(p) N-[1(R)-Carboxy-5-(1,3-dioxo-isoindolin-2-yl)pentyl]-α-(S)-(2-phenyl-ethyl)glycine-(L)-leucine, N-phenylamide;
(q) N-[1(R)-Carboxy-5-(1-oxo-isoindolin-2-yl)pentyl]-α-(S)-(2-phenyl-ethyl)glycine-(S)-leucine, N-phenylamide hydrochloride;
(r) N-[1(R)-Carboxy-5-(1-oxo-isoindolin-2-yl)pentyl]-α-(S)-(2-phenyl-ethyl)glycine-(S)-arginine, N-phenylamide;
(s) N-[1(R)-Carboxy-ethyl]-α-(S)-(2-(3-hydroxyphenyl)-ethyl)glycine-(S)-leucine, N-phenylamide hydrochloride;
(t) N-[1(R)-Carboxy-ethyl]-α-(S)-(2-(4-methylphenyl)-ethyl)glycine-(S)-leucine, N-phenylamide hydrochloride;

(u) N-[1(R)-Carboxy-ethyl]-α-(S)-(2-(2'-thienyl)ethyl) glycine-(L)-leucine, N-phenylamide;

(v) N-(1(R)-Carboxy-ethyl)-α-(S)-(2-(4-ethylphenyl) ethyl)glycine-(L)-leucine, N-phenylamide;

(w) N-[1(R)-Carboxy-5-(1-oxo-isoindolin-2-yl)pentyl]-α-(S)-(2-(4-propylphenyl)ethyl)glycine-(L)-leucine, N-phenylamide;

(x) N-(1(R)-Carboxy-ethyl)-α-(S)-(2-(4-chlorophenyl) ethyl)glycine-(L)-leucine, N-phenylamide;

(y) N-[1(R)-Carboxy-ethyl)]-α-(S)-(2-phenyl-ethyl)] glycine-α-(S)-(2-cyclohexyl-ethyl)glycine, N-phenylamide;

(z) N-[1(R)-Carboxy-ethyl)]-α-(S)-(2-phenyl-ethyl)] glycine-α-(S)-(cyclohexyl)glycine, N-phenylamide;

(aa) N-[1(R)-Carboxy-ethyl)]-α-(S)-(2-phenyl-ethyl)] glycine-α-(S)-(cyclohexylmethyl)glycine, N-phenylamide;

(ab) N-[1(R)-Carboxy-ethyl)]-α-(S)-(2-phenyl-ethyl) glycine-(L)-β-naphthylalanine, N-phenylamide;

(ac) N-[1(R)-Carboxy-ethyl)]-α-(S)-(2-phenyl-ethyl) glycine-(L)-α-naphthylalanine, N-phenylamide;

(ad) N-[1(R)-Carboxy-ethyl)]-α-(S)-(2-phenyl-ethyl) glycine-[(L)-glutamic acid, α, δ-bis-N-phenylamide];

(ae) N-[1(R)-Carboxy-ethyl)]-α-(S)-(2-phenyl-ethyl) glycine-(L)-leucine, N-cyclohexylamide;

(ae) N-[(1(R)-Carboxy-ethyl)]-α-(S)-(2-phenyl-ethyl) glycine-α-(S)-(4-hydroxyphenyl-ethyl)glycine, N-phenylamide;

(af) N-[1(R)-Carboxy-ethyl)]-α-(S)-(2-phenyl-ethyl) glycine-(L)-phenylglycine, N-phenylamide;

(ag) N-[1(R)-Carboxy-ethyl)]-α-(S)-(2-phenyl-ethyl) glycine-[(L)-glutamic acid, N$_\delta$-benzylamide, N$_\alpha$-phenylamide];

(ah) N-[1(R)-Carboxy-ethyl)]-α-(S)-(2-phenyl-ethyl) glycine-(L)-Ornithine, N-phenylamide;

(ai) N-[1(R)-Carboxy-ethyl)]-α-(S)-(2-phenyl-ethyl) glycine-(L)-arginine, N-phenylamide;

(aj) N-[1(R)-Carboxy-ethyl)]-α-(S)-(2-phenyl-ethyl) glycine-α-(S)-(3-phenylpropyl)glycine, N-phenylamide;

(ak) N-[1(R)-Carboxy-ethyl)]-α-(S)-(2-phenyl-ethyl) glycine-α-(S)-n-octylglycine, N-phenylamide;

(al) N-[1(R)-Carboxy-ethyl]-α-(S)-(2-phenyl-ethyl) glycine-(L)-Ieucine, N-(4-carboxyphenyl)amide;

(am) N-[1(R)-Carboxy-ethyl]-α-(S)-(2-phenyl-ethyl) glycine-(L)-Ieucine, N-(4-trifluoromethylphenyl) amide;

(an) N-[1(R)-Carboxy-ethyl]-α-(S)-(2-phenyl-ethyl) glycine-(L)-leucine, N-(3-pyridyl)amide;

(ao) N-[1(R)-Carboxy-ethyl]-α-(S)-(2-phenyl-ethyl) glycine-(L)-leucine, N-(benzothiazol-2-yl)amide;

(ap) N-[1(R)-Carboxy-ethyl]-α-(S)-(2-(4-n-propylphenyl)ethyl)glycine-(L)-leucine, N-phenylamide;

(aq) N-[1(R)-Carboxy-ethyl]-α-(S)-(2-(4-propylphenyl) ethyl)glycine-(L)-arginine, N-phenylamide;

(ar) N-[1(R)-Carboxy-ethyl]-α-(S)-(2-(3,4-dimethylphenyl-ethyl))glycine-(L)-leucine, N-phenylamide.

10. A pharmaceutical composition for treating a matrix metalloendoproteinase-mediated disease comprising a pharmaceutical carrier and a non-toxic effective amount of compound of formula I according to claim 9.

11. A pharmaceutical composition comprising a pharmaceutical carrier and 1 to 500 mg of compound of formula I according to claim 9.

12. A pharmaceutical composition comprising a pharmaceutical carrier and 1 to 500 mg of compound of formula I according to claim 1.

13. A method of inhibiting proteoglycan degeneration comprising the administration to a subject in need of such inhibition a therapeutically effective amount of a compound of Formula I according to claim 1.

14. A method of inhibiting proteoglycan degeneration comprising the administration to a subject in need of such inhibition a therapeutically effective amount of a compound of Formula I according to claim 1.

* * * * *